(12) United States Patent
Fedurco et al.

(10) Patent No.: US 7,704,543 B2
(45) Date of Patent: Apr. 27, 2010

(54) CONVERSION OF AMINE- TO CARBOXYL GROUPS ON SOLID SURFACES

(75) Inventors: Milan Fedurco, Geneva (CH); Anthony Romieu, Rouen (FR); Gerardo Turcatti, Geneva (CH)

(73) Assignee: Illumina Cambridge Limited, Nr. Saffron Walden (GB)

( * ) Notice: Subject to any disclaimer, the term of this patent is extended or adjusted under 35 U.S.C. 154(b) by 885 days.

(21) Appl. No.: 10/573,377

(22) PCT Filed: Sep. 27, 2004

(86) PCT No.: PCT/GB2004/004150

§ 371 (c)(1),
(2), (4) Date: Jul. 17, 2006

(87) PCT Pub. No.: WO2005/030695

PCT Pub. Date: Apr. 7, 2005

(65) Prior Publication Data

US 2007/0042109 A1    Feb. 22, 2007

(30) Foreign Application Priority Data

Sep. 25, 2003    (EP)    ................................. 03021777

(51) Int. Cl.
*G01N 1/28*    (2006.01)
*C12M 1/34*    (2006.01)

(52) U.S. Cl. .................. 427/2.11; 435/287.2; 536/25.3; 548/126; 548/334.1; 556/436

(58) Field of Classification Search ............... 536/25.3; 435/287.2; 427/2.11; 548/126, 334.1; 556/436
See application file for complete search history.

(56) References Cited

U.S. PATENT DOCUMENTS

| 4,140,662 | A | | 2/1979 | Reckel et al. |
| 6,043,353 | A | * | 3/2000 | Pon et al. ................... 536/25.3 |
| 6,319,674 | B1 | | 11/2001 | Fulcrand et al. |
| 2002/0076723 | A1 | * | 6/2002 | Virtanen ....................... 435/6 |

FOREIGN PATENT DOCUMENTS

EP    0 280 840    9/1988

OTHER PUBLICATIONS

Leung et al., Synthesis and binding properties of cyclodextrin trimers, Tetrahedron Letters, 42:6255-6258 (2001).
Podlaha et al., Crystal structure of 1, 2, 3, 4, 5, 6-hexakis (2'-carboxyethyl) benzene dehydrate, $C_{24} H_{30} O_{12} \cdot 2H_2O$, Fur Kristallographie-New Crystal Structures, 214:183-184 (1999).
Spino et al., Lanthanide catalysts for the hetero Diels-Alder reaction: effect of ligand structure and acidity, Canadian Journal of Chemisty, 75:1047-1054 , 1997.
Collman et al., Synthesis an Characterization of the "Pocket" Porphyrins[1a], J. American Chemical Socity, 105:3038-3052 (1983).
Kanishi et al., Synthesis of macrocyclic [n.n.n.] (1, 3, 5) cyckophane polylactones , Bulletin of the Chemical Society of Japan, 54:3828-3831 (1981).
Sigman et al., Cobalt-Catalyzed Cyclotrimerization of Alkynes in Aqueous Solution, J. Am. Chem. Soc., 120:5130-5131 (1998).
Hoffmann et al., Synthesis, 3:237-239 (1982).
Hopff et al., Helv. Chim. Acta, 40:274-280 (1957).
Colquhoun et al., One-step syntheses of very large cage-type molecules from aromatic subunits, Chem. Commun, 2574-2575 (2001).
Newman et al., The Synthesis of 1, 3, 5-Benzenetriacetic Acid by a Triple-Willgerodt Reaction, J. Am. Chem Soc., 76:6196-6197 (1954).
Wenkert et al., Derivatives of Hemimellitic Acid. A Synthesis of Erythrocentaurin, J. Am. Chem. Soc., 29:2534-2542 (1964).
"Aldrich-Handbuch Feinchemikalien", 179-180(1999).
Hanessian et al., Design and synthesis of a cephalosprrin-carboplatinum prodrug activatable by a β-lactamase, Can J. Chem., 71:896-906, (1993).
Pirrung et al., A General Method for the Spatially Defined Immobilization of Biomolecules on Glass Surfaces Using "Caged" Biotin, Bioconjugate Chemistry, 7:317-321 (1996).
Adessi et al., Solid phase DNA amplification: characterization of primer attachment and amplification mechanisms, Nucleic Acids Research, 28:e87 (1-8) (2000).
Pirrung, How to Make a DNA Chip, Angew. Chem. Int. Ed., 41:1276-1289 (2002).

* cited by examiner

*Primary Examiner*—Shailendra Kumar

(57)    ABSTRACT

This invention provides a new method of obtaining a high density, reproducible and uniform coverage of a solid surface, compounds suitable for such a method and methods of preparing such compounds. This invention further relates to methods of the chemical modification (carboxylation) of solid surfaces and their subsequent use for the attachment of amine-containing molecules including DNA, proteins and other polymers.

35 Claims, 11 Drawing Sheets

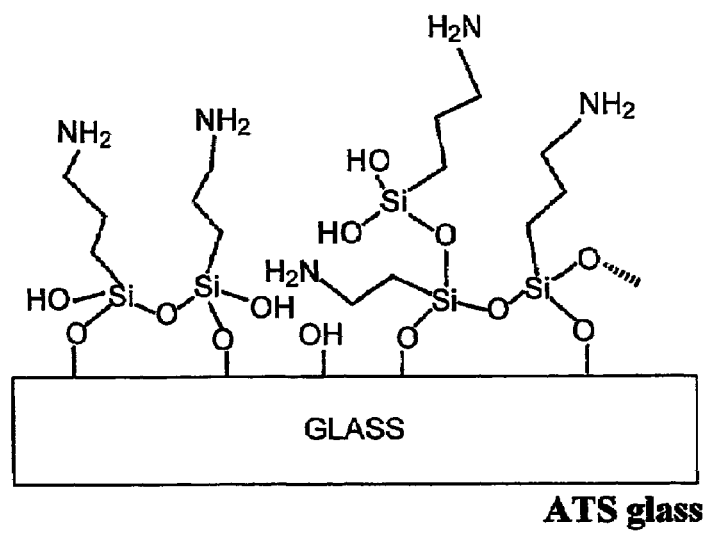
ATS glass
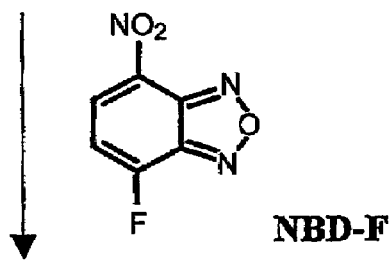
NBD-F
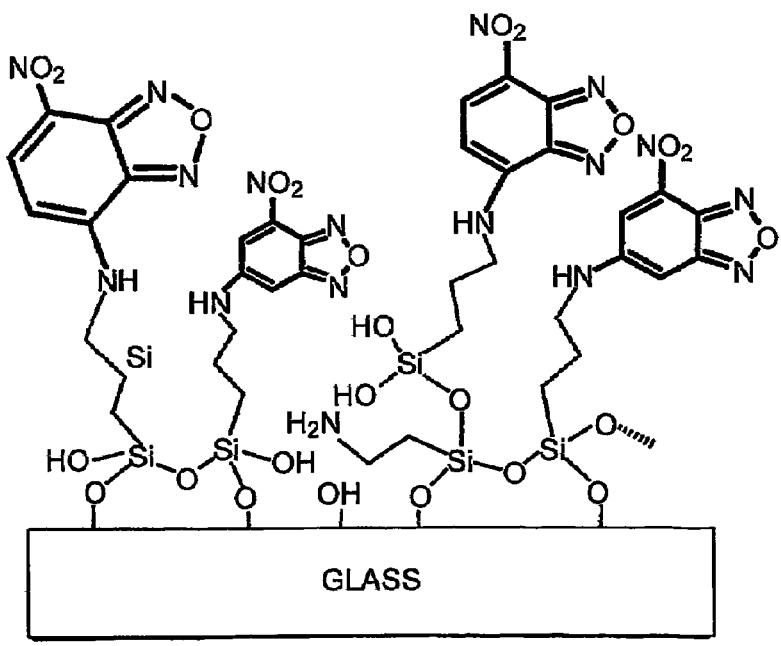
FIG. 4      NBD-stained ATS glass

SEQUENCE LISTING

<160> NUMBER OF SEQ ID NOS: 4

<210> SEQ ID NO 1
<211> LENGTH: 34
<212> TYPE: DNA
<213> ORGANISM: Artificial
<220> FEATURE:
<223> OTHER INFORMATION: synthetic construct PRIMER 10T-P1

<400> SEQUENCE: 1
tttttttttt caccaaccca aaccaaccca aacc                    34

<210> SEQ ID NO 2
<211> LENGTH: 33
<212> TYPE: DNA
<213> ORGANISM: Artificial
<220> FEATURE:
<223> OTHER INFORMATION: synthetic construct PRIMER 10T-P2

<400> SEQUENCE: 2 ttttttttttg aggaaaggga agggaaagga agg                    33

<210> SEQ ID NO 3
<211> LENGTH: 24
<212> TYPE: DNA
<213> ORGANISM: Artificial
<220> FEATURE:
<223> OTHER INFORMATION: synthetic construct PRIMER REVERSEP1-TEXAS RED

<400> SEQUENCE: 3
ggtttgggtt ggtttgggtt ggtg                               24

<210> SEQ ID NO 4
<211> LENGTH: 24
<212> TYPE: DNA
<213> ORGANISM: Artificial
<220> FEATURE:
<223> OTHER INFORMATION: synthetic construct PRIMER REVERSE-P2-TEXAS RED

<400> SEQUENCE: 4
ccttcctttc ccttcccttt cctc                               24

CONVERSION OF AMINE- TO CARBOXYL GROUPS ON SOLID SURFACES

CROSS REFERENCE TO RELATED APPLICATIONS

The present application is a National Stage Application claiming the priority of co-pending PCT Application No. PCT/GB2004/004150 filed Sep. 27, 2004, which in turn, claims priority from European Application Serial No. 03021777.2, filed Sep. 25, 2003. Applicants claim the benefits of 35 U.S.C. §120 as to the PCT application and priority under 35 U.S.C. §119 as to the said European application, and the entire disclosures of both applications are incorporated herein by reference in their entireties.

NATURE OF THE INVENTION

1. Field of the Invention

This invention relates to methods of the chemical modification (carboxylation) of solid surfaces and their subsequent use for the attachment of amine-containing molecules including DNA, proteins and other polymers.

2. Prior Art

A variety of methods have been reported for the covalent attachment of biomolecules (including DNA and proteins) to a solid surface (such as glass slide, fused silica, gold and silicon wafers). Typically, such type of immobilization involves the reaction of an active functional group on the biomolecule with an activated functional group on the solid surface. Other reactions, such as UV cross-linking, can be used for covalent attachment but are not functional group type-specific.

For silicon oxide based surface, the functionalization is performed by coating with a bifunctional organosilane, i.e., organosilane having a first functional group enabling covalent binding to the surface (often an Si-halogen or Si-alkoxy group, as in $-SiCl_3$ or $-Si(OCH_3)_3$, respectively) and a second functional group to react with the functional group of a given biomolecule (often an aldehyde, amino or carboxyl group). Interestingly, the functional group (introduced by the silanization step) can be modified by using single- or multi-step synthetic procedures to provide a wide range of reactive groups on the surface, such as N-acylimidazole, 2- or 3-bromoacrylate, cyanuric chloride, disulfide, N-hydroxysuccinimide ester, hydrazide, iodoacetyl, imidoester, isocyanate, isothiocyanate, maleimide, succinimidyl carbonate, suitable for further reactions with biopolymers under the mildest conditions possible.

Alternatively, the derivatization of gold surfaces (which is not possible by silanization) requires the creation of a multilayer structure (starting with mercaptoalkanoic acid) which adsorbs poly(L-lysine) electrostatically. Subsequently, chemical modifications of the amino side-chains of this biopolymer provides a suitable support suitable for covalent bonding of biomolecules. However, the known procedures present a major drawback: the almost exclusive use of bifunctional cross-linkers for surface activation dramatically affects the surface properties (loading capacity, charge, hydrophilic or hydrophobic character) and thus the quality and performance of the resulting biopolymer-arrays. Indeed, it is difficult to avoid the side-reactions of reticulation and hydrolysis of such crosslinking agents occurring during the synthesis process (functionalization of the solid support, storage, or during the immobilization of biomolecules) which significantly decrease the loading of the support. Alternative methods which involve either the in situ synthesis or the attachment of a preformed dendrimeric linker to the surface enable to increase both the reactive group loading and biomolecule density. However, such derivatizations require multi-step reactions which are often time-consuming and use unstable reagents such as chloroformates and acid chlorides. These reagents are not compatible with use in closed volumes, which prevents use of such derivatization methods in microfluidic devices. Furthermore, the functional group density (and the biomolecule density) also controls the number and the nature of charges eventually present at neutral pH on the surface. Dependent on the type of biopolymer-array, this could strongly influence its performances especially by enhancing the non-specific binding of biopolymers.

Consequently, a significant amount of batch to batch variability is obtained. This is often not acceptable because there is a significant impact on the accuracy and reproducibility of quantitative determinations. For such determinations, it is important to be able to prepare arrays that show consistency in the performance of the array particularly from one batch to the next.

The present invention is directed to the aforementioned need in the art and provides a new method of obtaining a high density, reproducible and uniform coverage of a surface while avoiding the aforementioned problems and difficulties associated with the procedures in the art.

OBJECT OF THE INVENTION

It is therefore an object of the invention to provide linker compounds and the use thereof in methods for the derivatization of solid surfaces based on the conversion of the surface amine to carboxyl group(s). Another object of the invention is to avoid the use of organosilanes bearing protected carboxylic group and their deprotection as mode of introduction of free carboxylic groups to the glass surface. A further object of the invention is to provide a method for the selective attachment of molecules to such patterned surfaces. Further objects will be apparent from the subject matter of the claims.

BRIEF DESCRIPTION OF THE INVENTION

The above technical problem is solved by the provision of a compound of the general formula (I)

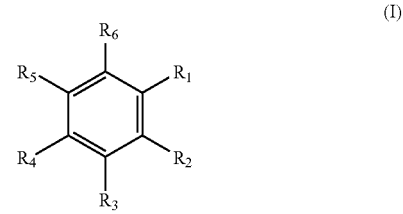

(I)

wherein at least three of $R_1$ to $R_6$ are, independent from each other, selected from
$-(CH_2)_n-(C=O)-X-Y-Z$, and the remaining R groups are H;
or $R_1$ and $R_2$ form a ring, preferably an anhydride;
X is a group selected from $C_1$-$C_{10}$ alkyl, $C_1$-$C_{10}$ alkenyl, a $C_3$-$C_8$ cycloalkyl, aryl, heteroaryl, or a polyethylene glycol chain of the general form $(CH_2-CH_2-O)_m$, wherein m is an integer from 1 to 450, or X is a bond;
Y is a carbonyl group, or a bond;
Z is OH or an electron withdrawing group; and
n is an integer from 0 to 10.

Alternatively, in the compound of general formula (I):
(i) at least three of $R_1$ to $R_6$ are, independent from each other, selected from —$(CH_2)_n$—(C=O)—X—Y—Z and the remaining R groups are H; or
(ii) $R_1$ and $R_6$ are together of formula —(C=O)—Z'—(C=O)— so as to form a ring, at least one of $R_2$ to $R_5$ are, independent from each other, selected from —$(CH_2)_n$—(C=O)—X—Y—Z and the remaining R groups are H;

X is a group selected from $C_1$-$C_{10}$ alkyl, $C_1$-$C_{10}$ alkenyl, a $C_3$-$C_8$ cycloalkyl, aryl, heteroaryl, or a polyethylene glycol chain of the general form $(CH_2$—$CH_2$—$O)_m$, wherein m is an integer from 1 to 450, or X is a bond;

Y is a carbonyl group, or a bond;

Z is OH or an electron withdrawing group;

Z' is O or S; and n is an integer from 0 to 10.

Preferably Z' is oxygen so as to form an anhydride ring.

The above compound is useful in methods for surface modification. The method described herein replaces traditional glass silanization by organosilane molecules bearing protected carboxylic group by direct carboxylation of aminosilanated glass.

The present invention provides a highly efficient and fast method for glass carboxylation making use of activated carboxylic acids in the presence of commonly used bulk catalysts. The method presented herein allows for cost-effective scale up of glass carboxylation avoiding the need for the deprotection of siloxane films and, therefore, film inhomogeneities which might result from such deprotection.

Carboxylation of solid surfaces according to the present invention is not limited to glass but can be extended to amine-terminated polymers, metals, semiconductors, insulators and other solid supports.

Carbodiimide-mediated DNA grafting on carboxyl-terminated glass prepared according to the present invention allows one to obtain high surface densities of 5'-aminated DNA primers. In a preferred embodiment, such high densities permit achieving efficient solid-phase DNA amplification and generation DNA colonies.

ADVANTAGES OF THE INVENTION

Chemical modification of glass surfaces becomes increasingly important in light of its applications in various fields of chemistry, biology and medicine. Glass is known for its relative inertness in respect to biomolecules, excellent stability in a wide range of organic solvents and high optical transparency in the visible range. However, in general, chemical modification of glass surface is considered as more demanding than that of noble metals relying, for example, on self-assembly. One of commonly used methods for the chemical modification of glass is based on its silanization. Organosilane molecule used to silanize glass surface contains at one of its extremities a functional group reacting with the glass surface (Si-bearing moiety) while, at the other end, a group which allows to covalently attach a given molecule to the glass surface is present. For example, covalent coupling of proteins, or aminated DNA, can be achieved through the formation of the peptidic bond between the carboxyl group of the surface siloxane and amino group(s) of a given biomolecule (or vice versa). Such immobilization reactions may be catalyzed by common bulk catalysts and are usually fast and relatively robust. Preparation of highly carboxylated solid surfaces is of special interest to many technologies in the above mentioned fields.

Because of the very low stability of certain organosilane molecules towards hydrolysis, the functional group to be used for the attachment DNA (or protein) to glass is usually present in "protected" form. Typical example of the latter being acetoxypropyl-trimethoxysilane. Under specific conditions, this organosilane molecule is allowed to react with hydroxyl-terminated glass surface and form COOEt-terminated siloxane film. However, deprotection of the surface ester film and formation of free carboxylic groups requires prolonged glass treatment in strong acids (i.e., 50% $H_2SO_4$ in ethanol, 12 hours). This often leads to only partial deprotection of surface ester groups and, in addition, might lead to some damage of the siloxane film (hydrolysis). In order to avoid such problems, we have developed a novel approach to glass carboxylation based on chemical derivatization of aminosilanated glass by organic carboxylic acids.

Reactivity of amines with activated carboxylic acid is well known in prior art and is exploited in organic synthesis, chemical modification of proteins as well as in the chemical modification of solid surfaces. One of common strategies in the case of glass modification is to treat aminosilanated glass surface with a so-called "bifunctional linker" possessing on one end of the molecule the activated group capable of reacting with the surface amino groups, while the other extremity is available for the reaction(s) with solution species of interest. Covalent coupling of biomolecules to the glass surface modified with bifunctional linker normally proceeds in a two separate stages. In the first step, silanized glass is reacted with the reagent forming a monolayer (or sub-monolayer) which introduces to the glass a certain reactivity towards solution species (i.e., DNA, or protein). In the second step, immobilization of the solution species to the activated glass surface can be achieved either spontaneously and/or thermally, photochemically, or by other methods known in the art. The main disadvantages of activated "bifunctional linkers" are: relatively low chemically stability of coupling reagents towards hydrolysis, relatively high cost, slow reaction kinetics and relatively high bulk concentrations of solution species required in order to drive the immobilization reaction on solid surface to its completion. Another disadvantage of "bifunctional linkers" is that aliphatic acids having —COOH group at both extremities of the aliphatic chain are relatively flexible so that both of the activated carboxylic groups may react with the amine-terminated surface. This is likely to introduce a certain degree of hydrophobicity to the solid surface and could lead to decrease in the amount of free carboxyl groups available for the covalent attachment of biomolecules to the solid surface.

The present invention is based on bulk catalyst-mediated covalent attachment of "tri-functional linkers" based on tri-carboxylic acid to the aminosiloxane-modified glass surface (FIG. 1) followed by carbodiimide-catalyzed immobilization of amine-containing DNA to the glass surface (FIG. 2). Preferred aromatic trifunctional compounds used herein are benzene-1,3,5-triacetic acid (BTA) and trimesic acid (TMA). The main advantages when using these aromatic molecules over aliphatic bicarboxylic acids is that even though two carboxylic groups of the aromatic linker molecule may react with the surface amino groups, one —COOH would still remain available for the immobilization biomolecules to the solid surface. One important advantage of the present invention is the fact that it relies on bulk catalysis for both, glass carboxylation as well as covalent coupling of the aminoalkyl-substituted DNA to carboxyl-terminated surface. This in turn results in a more robust chemistry as compared to classical methods relying exclusively on the use of bifunctional linkers.

Conversion of amine-to-carboxyl-terminated siloxane surface according to the present invention is ideally suited for grafting the aminated DNA in microfluidic devices. In this respect, BTA-modified glass represents apparent advantage as compared to aldehyde chemistry requiring borohydride reduction step, which leads to violent formation of hydrogen bubble (not compatible with reactions taking place in closed volumes).

Yet another advantage of BTA-derivatized glass is relatively high specificity (>80%) of DNA grafting via 5' amino end. In this respect, BTA performs better than phenelyneisothiocyanate (PITC)-modified aminosiloxane glass. The surface densities of grafted 5'amino-DNA on BTA glass exceed greatly those obtained on maleimide (MBS)- or PITC-modified aminosiloxane glass. This is especially important for applications such as solid-phase DNA amplification and DNA colony.

UTILITY OF THE INVENTION

Among other applications, carboxylated glass may be used as a support for the construction of molecular libraries, for the fixation of supramolecular complexes (complex-complex recognition), for the immobilization of optically active molecules and in the solid phase synthesis of DNA and proteins. Carboxylated glass slides may be exploited in the solid-phase DNA amplification, DNA sequencing, construction of DNA chips, protein arrays and various types of sensors with applications ranging from every day life to medicine.

Solid surfaces chemically modified according to the present invention can be used to modify physico-chemical properties of solid surfaces including their surface tension, surface charge, index of refraction, linear and/or non-linear optical properties, surface conductivity, chemical resistance of the material, and others. Carboxylated glass beads can be used for separation of molecular and ionic species (in ion-exchange columns) and, importantly, are expected to show increased chemical stability in organic solvents as compared to carboxyl-containing polymers currently used for such purpose. Positively charged molecules may interact electrostatically with negatively charged carboxylated surfaces and, therefore, can be pre-concentrated on solid surfaces (for example, metallic electrodes) for their subsequent analytical detection (for. example, for in vivo monitoring of neurotransmitters in brain, and others).

Carboxylated glass, and other carboxylated substrates prepared as described herein, may be used for the covalent attachment of biomolecules including living cells and their constituents such as proteins, DNA, peptides, vitamins and others. Patterned —COOH/—NH$_2$ or —COOH/—OH glass surfaces prepared as described below can be designed to bind preferentially certain species having complementary charge to the ionized groups present on the surface. Such mixed monolayers might be used for tuning of the strength of electrostatic interactions between a given biomolecule (DNA, protein and others) and chemically-modified solid surface. Mixed films having varying surface charge but pertaining still very high degree of hydrophilicity may find applications in the construction of microfluidic devices relying on separation of molecules depending on their size and charge. For example, as described in the present invention, carboxylate-terminated glass surface may be diluted with terminal hydroxyl groups. This in turn should affect not only the efficiency of catalyst-mediated covalent coupling of a given biomolecule to a glass surface but also its adsorptivity at the solid/liquid interface. It is well recognized that the adsorption of a given biomolecule will be quite different on —COO$^-$/NH$_3^+$ as compared to —COO$^-$/—OH modified glass surface.

Derivatization of aminated surfaces according to the present invention can be extended to conducting and non-conducting surfaces such as metals chemically modified with amine-terminated monolayers (or multilayers), electronically conducting polymers, insulating polymers, and others, providing these contain any reactive groups capable of reacting with the activated carboxylic group(s) (i.e., esters, acyl halides, and others). In the latter case, polymers having modified ion-exchange properties, electronic conductivity, solubility in water (or some other solvents), having novel optical and mechanical properties may be prepared.

Some other applications of carboxylated solid surfaces are in the surface catalysis, for example, in the solar energy conversion (fixation of dyes on semiconductor surfaces), in the modification of amine-terminated thiol monolayers on metal surfaces, or in the attachment of colloidal particles to various solids forming the covalent bond.

It is recognized that the subsequent chemical modification of carboxylated surfaces can be used to introduce to solid/liquid or solid/gas interface wide range of physico-chemical properties and can be used for numerous applications which will become more clear from examples described in the present invention.

LEGEND TO FIGURES

Figure 3:
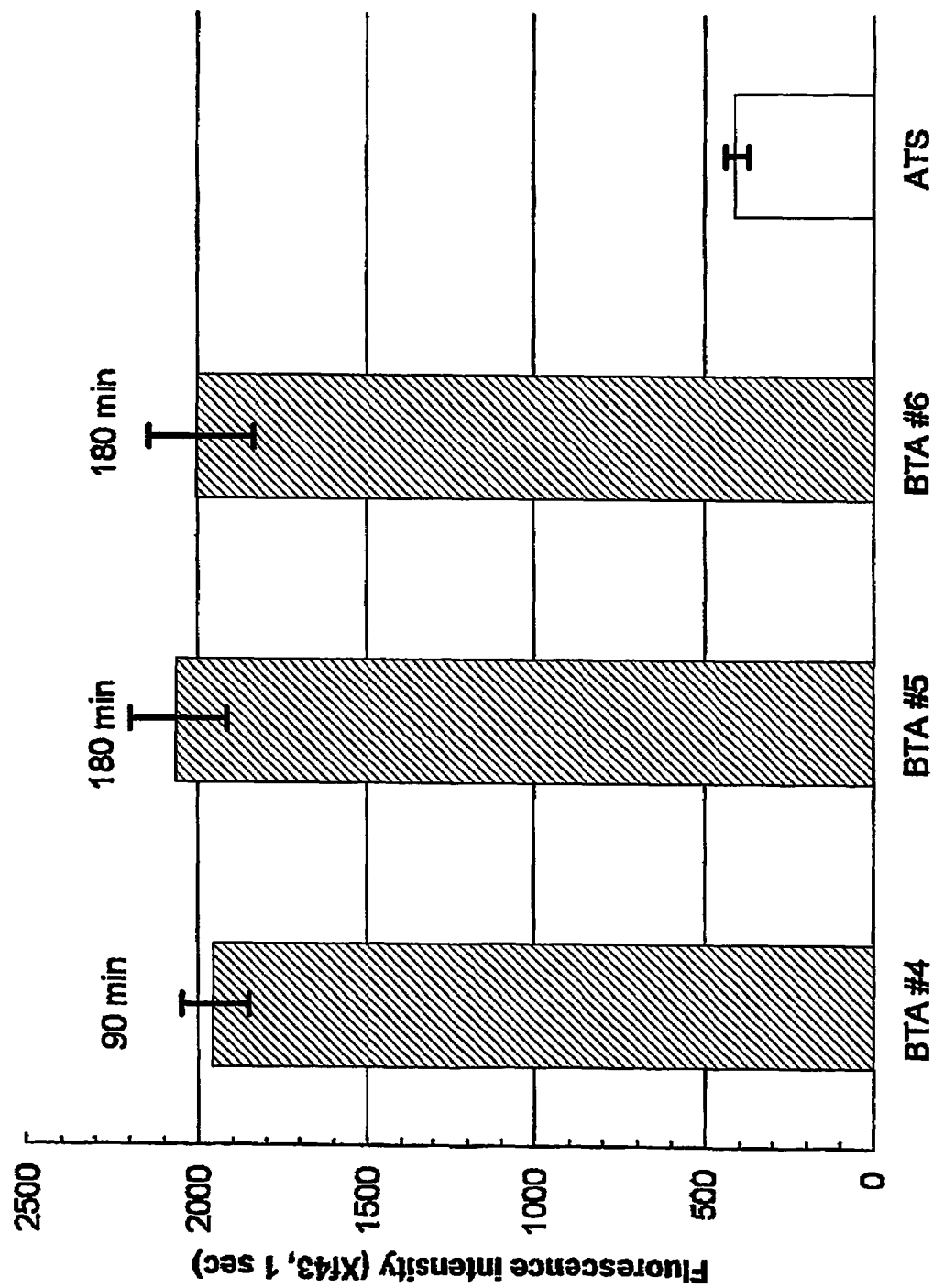
Figure 5:
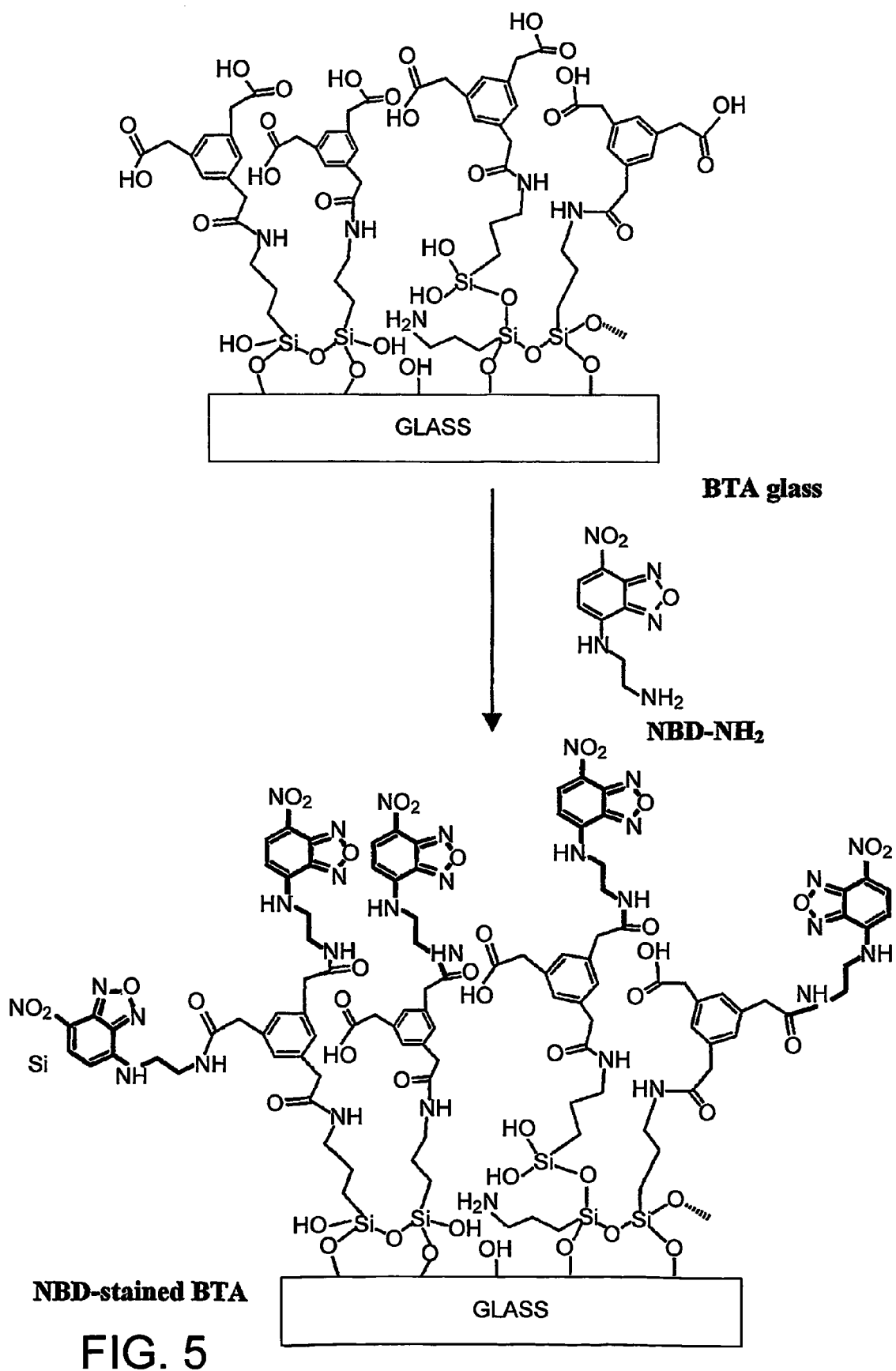
Figure 6:
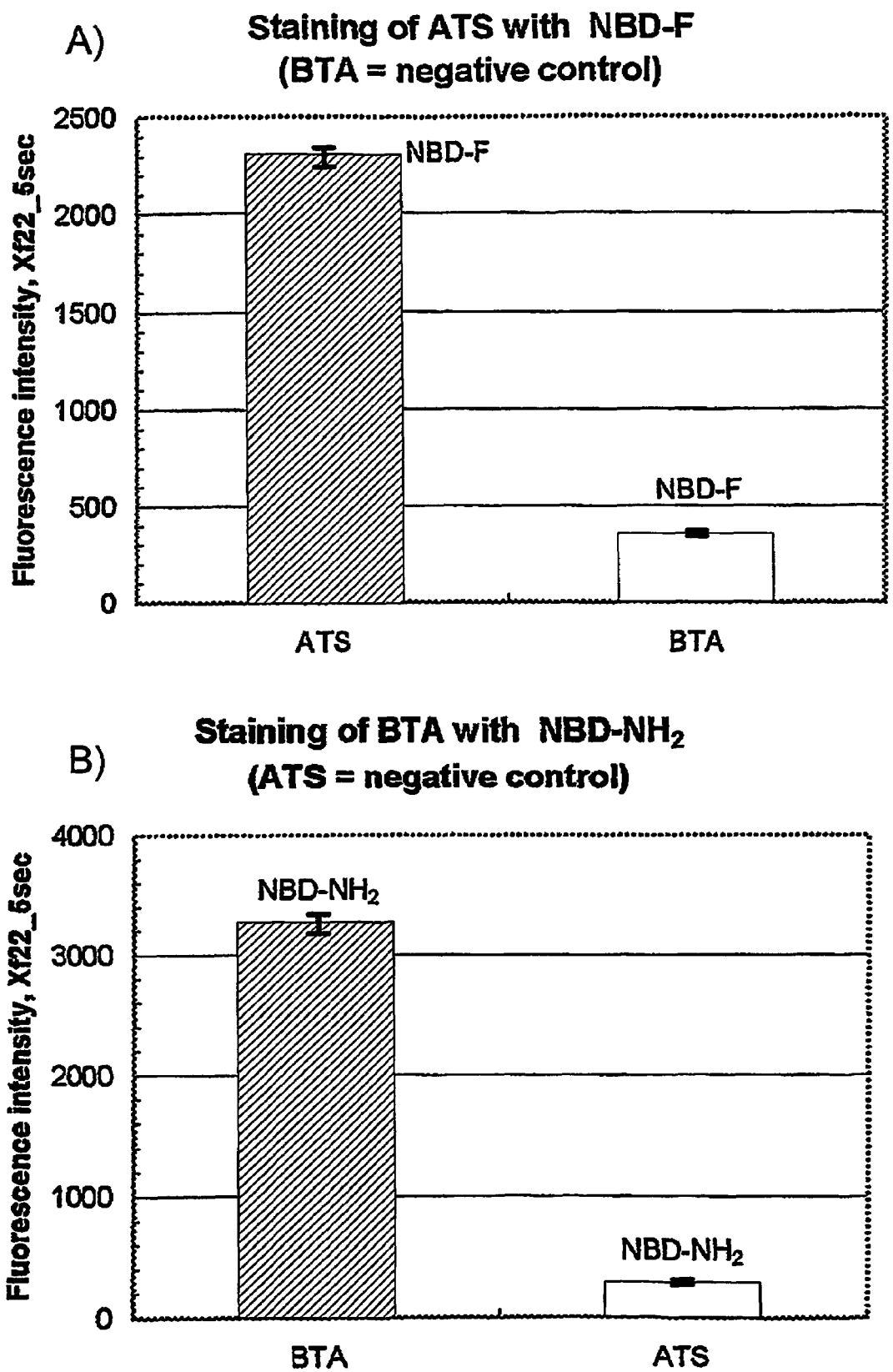
Figure 7:
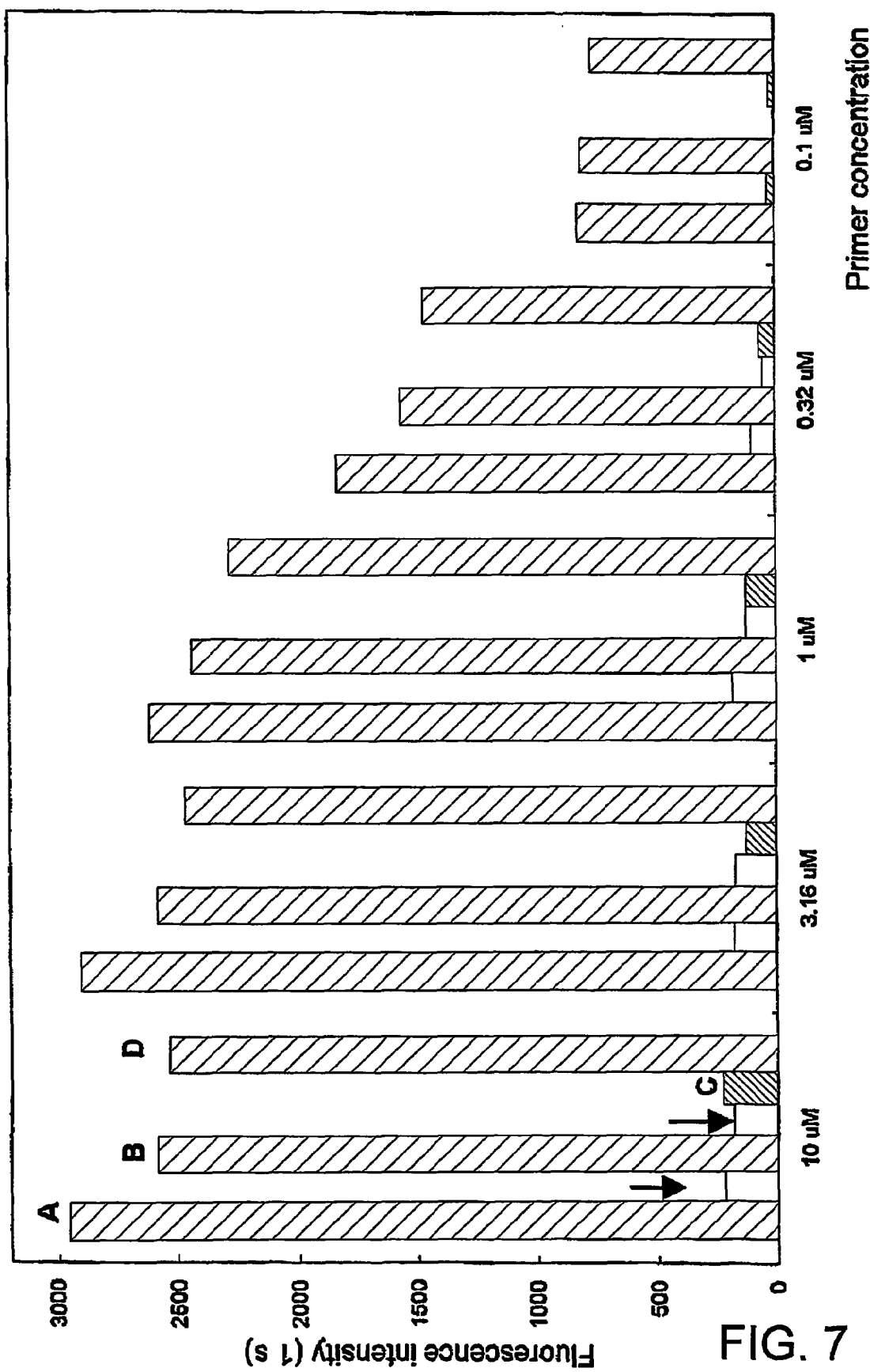

FIG. 3 shows the fluorescence signal due to the covalent coupling of the amino-Texas Red to carboxyl-terminated BTA slides. ATS represents staining of aminosilanated slide (negative control). Time of the carboxylation of ATS slides by BTA(NHS)2 COOH is indicated in the figure. Staining: amino-Texas Red (40 μg per slide), BOP (1 eq. per compound 5), DIEA (3 eq. per compound 5), in DMSO/DMF (9:1 v/v), RT, 1 hour;

FIG. 4 shows the fluoride group of the NBD-F reacting with the amino group of ATS resulting in a covalent attachment of the fluorescent dye to the glass surface;

FIG. 5 shows the amino group of NBD-NH2 reacting with BOP-activated carboxyl group on BTA, which results in covalent attachment of the fluorescent dye to the glass surface;

FIG. 6 shows an example of staining of aminosilanized (ATS) slides with 4-fluoro-7-nitrobenzofurazan (NBD-F) and of BTA slides with (7-nitrobenzo-2-oxa-1,3-diazol-4-yl) ethylenediamine (NBD-NH2) with corresponding negative controls. Fluorescence of NBD-modified slides was measured in the air;

FIG. 7 shows three successive hybridizations (A, B, D) of the Texas Red-labeled reverse-P1 primer (500 nM) shown for various bulk concentrations of 5' amino-10T-P1 primer (34-mer) grafted on BTA glass. Texas Red-labeled primer (hatch shaded) having a non-complementary sequence (C) did not hybridize to the grafted primer.

Figure 8:
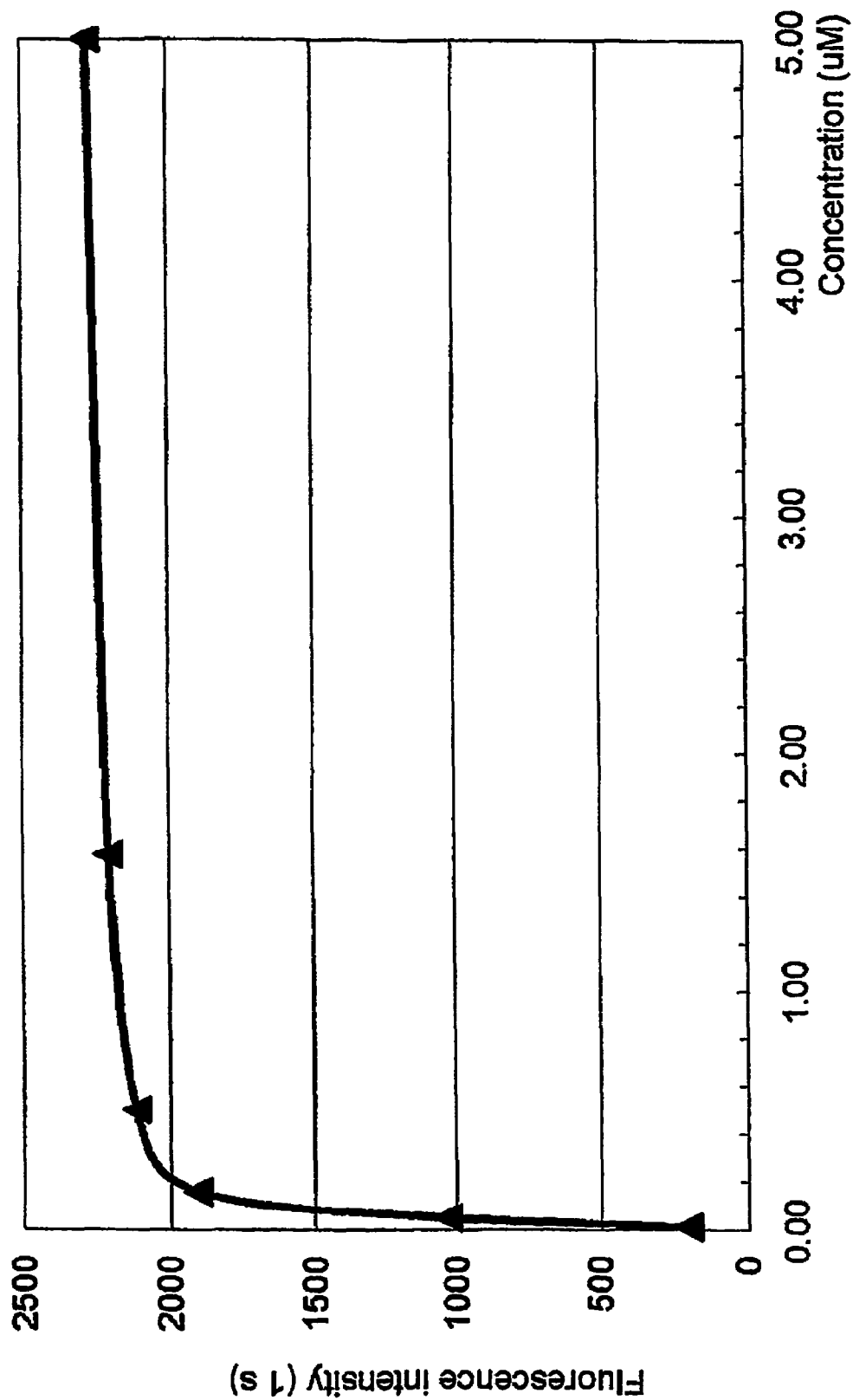

Grafting conditions: 10 mM EDC/10 mM MeImz (50° C.), 1 hour. Background subtracted;

FIG. 8 shows the concentration dependence for the grafting of 5' amino-10T-P2 primer (34-mer) on BTA glass. Grafting conditions: 10 mM EDC/10 mM MeImz (50° C.)/1 hour. Hybridization: 500 nM reverse-P2-Texas Red in TMN buffer.

Figure 9:
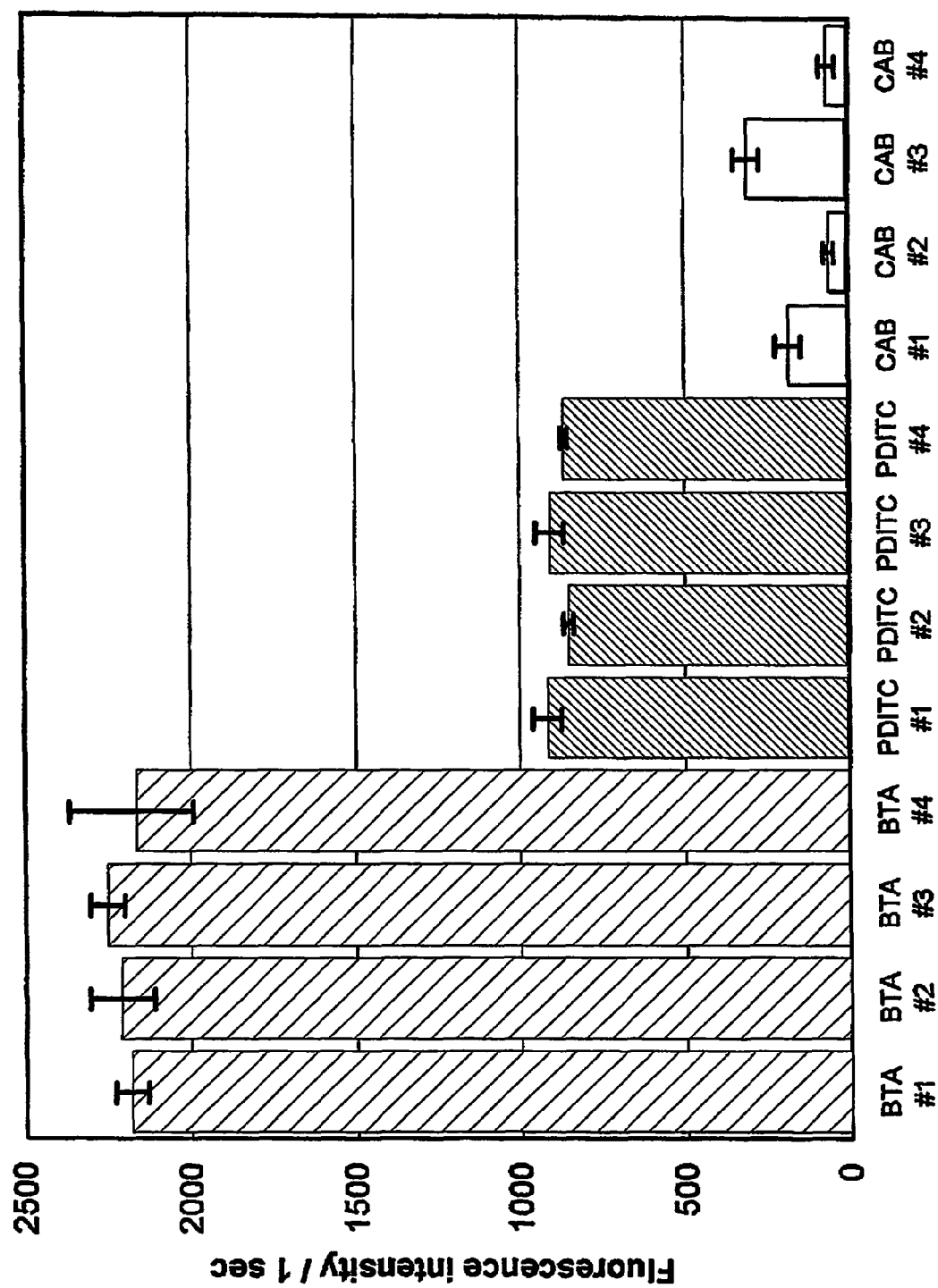
Figure 10:
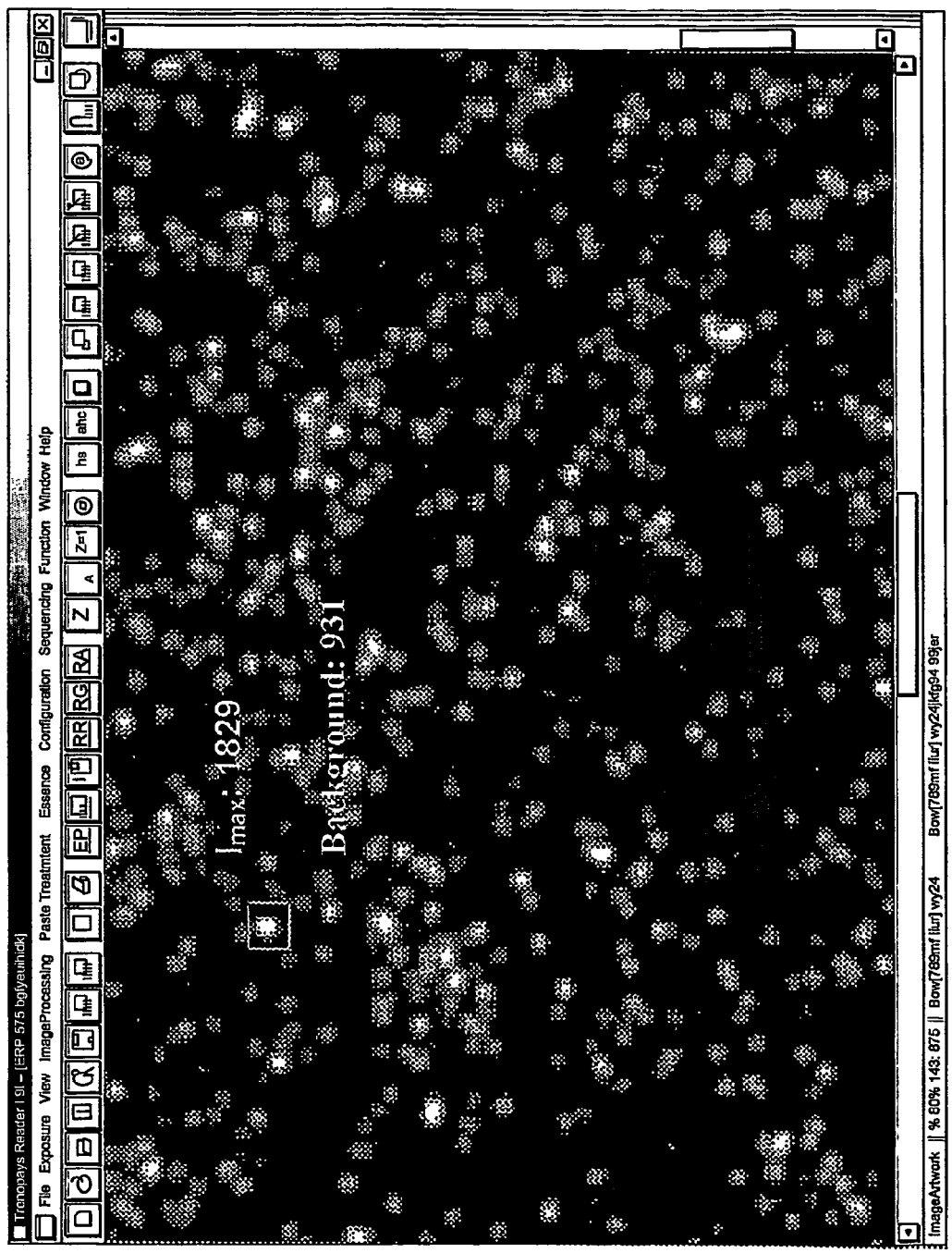

Experimental data points are connected with a solid line to guide the eye. Background subtracted;

FIG. 9 shows the hybridization signal for 5'-amino-P2 primer grafted on:

A) BTA glass (BTA #1-4, black) B) aminosilanized slides reacted with phenylene isothicyanate (PDITC #1-4, stripes) and C) commercially available carboxyl-terminated slides CAB-25C from CEL Associates (CAB #1-4, white). Grafting conditions: 1.0 µM primer, 10 mM EDC/10 mM MeImz, 50° C./1 hour. Hybridization: 500 nM reverse-P2-Texas Red. Background subtracted; and FIG. 10 shows SYBR GreenI-stained thermocycled DNA colonies formed in all glass-made microfluidic device derivatized with BTA. Channels of the chip were aminosilanized, reacted with active ester of BTA and hydrolyzed to form highly carboxylated glass surface.

Grafting conditions: 300 PM 5'-amino-Px, 700 PM 5'-amino-Py. Template: 50 pM 5'-amino-Template (359 bp). 10 mM EDC/10 mM MeImz, 50° C./30 min.

Amplification: 0.025 U/µl Taq DNA polymerase (Amersham), Taq buffer (1x), 200 µM dNTP, 1% DMSO, 1M betaine (40 cycles: 95° C./45 sec, 58° C./90 sec and 72° C./90 sec).

Staining: SYBR GreenI (diluted 10000-fold) in TE buffer/ 10 minutes.

The present invention will now be further described. In the following passages different aspects of the invention are defined in more detail. Each aspect so defined may be combined with any other aspect or aspects unless clearly indicated to the contrary. In particular any feature indicated as being preferred or advantageous may be combined with any other feature or features indicated as being preferred or advantageous.

DETAILED DESCRIPTION OF INVENTION

The methods of the present invention provide derivatization methods for the conversion of amino groups to carboxyl groups on solid surfaces. The methods of the present invention further provide for chemical methods allowing to quantify the efficiency of such conversion. Specifically, the carboxylation of the surface is achieved by coupling an organic molecule containing two, three, or more carboxylic groups (polycarboxylic acid derivative) to the amino layer. Such reaction requires either the use of a reactive derivative of polycarboxylic acid (i.e., anhydride, acyl halide or active ester) or a coupling reagent (such as carbodiimide, uronium or phosphonium salt) which formally acts as dehydrating agent between carboxylic acid and amine by generating highly reactive intermediates.

The linker of the present invention is a compound of the general formula (I):

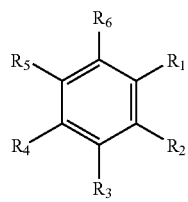

(I)

wherein at least three of $R_1$ to $R_6$ are, independent from each other, selected from —$(CH_2)_n$—(C=O)—X—Y—Z, and the remaining R groups are H; or $R_1$ and $R_2$ form a ring, preferably an anhydride;

X is a group selected from $C_1$-$C_{10}$ alkyl, $C_1$-$C_{10}$ alkenyl, a $C_3$-$C_8$ cycloalkyl, aryl, heteroaryl, or a polyethylene glycol chain of the general form $(CH_2$—$CH_2$—$O)_m$, wherein m is an integer from 1 to 450, or X is a bond;

Y is a carbonyl group, or a bond;

Z is OH or an electron withdrawing group; and n is an integer from 0 to 10.

The linker of the present invention may also be a compound of the general formula (I) wherein i) at least three of $R_1$ to $R_6$ are, independent from each other, selected from —$(CH_2)_n$—(C=O)—X—Y—Z and the remaining R groups are H; or (ii) $R_1$ and $R_6$ are together of formula —(C=O)—Z'—(C=O)— so as to form a ring, at least one of $R_2$ to $R_5$ are, independent from each other, selected from —$(CH_2)_n$—(C=O)—X—Y—Z and the remaining R groups are H;

X is a group selected from $Cl_1C_{10}$ alkyl, $C_1$-$C_{10}$ alkenyl, a $C_3$-$C_8$ cycloalkyl, aryl, heteroaryl, or a polyethylene glycol chain of the general form $(CH_2$—$CH_2$—$O)_m$, wherein m is an integer from 1 to 450, or X is a bond;

Y is a carbonyl group, or a bond;

Z is OH or an electron withdrawing group;

Z' is O or S; and n is an integer from 0 to 10.

Preferably, for the at least three of $R_1$ to $R_6$ n=0, and the remaining R groups are H, more preferably, the at least three of $R_1$ to $R_6$ are $R_1$, $R_3$ and $R_5$.

According to a preferred embodiment, for the at least three of $R_1$ to $R_6$ n=1, and the remaining groups are H, more preferably, the at least three of $R_1$ to $R_6$ are $R_1$, $R_3$ and $R_5$.

Preferably, for each of the at least three of $R_1$ to $R_6$ n is an integer from 2 to 5, and the remaining groups are H, preferably, the at least three of $R_1$ to $R_6$ are $R_1$, $R_3$ and $R_5$.

Z is OH or any group that activates the carbonyl towards nucleophilic displacement by S—$NH_2$ without being incorporated into the final carboxylated surface.

Typically, Z is a good leaving group, selected so as to make an activated derivative of carboxylic acid. Z is optionally an anhydride that links two adjacent carboxylic acid functions (only possible when n=0 and both X and Y are nothing, see general formula II) or an halogen atom (F, Cl, Br) yielding highly reactive derivatives.

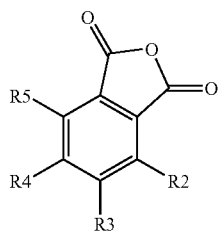

General Formula II

Put another way Z may be a good leaving group selected so as to make an activated derivative of carboxylic acid. Z may be a halogen atom such as F, Cl, Br or I, preferably F, Cl or Br. Where the compounds of general formula (I) are defined so as to make reference to the present of Z', Z' is preferably oxygen thereby providing compounds of general formula (II) above.

Z is alternatively cyanomethyl, hydroxysuccinimide (or its sodium sulfonate derivative, NHS or sulfo-NHS), hydroxyphthalimide, hydroxypiperidine or phenol (that is further substituted by at least one strong electron withdrawing group (EWG) such as chloro, fluoro or nitro) to give isolable activated esters which are generated by activation of carboxylic acids with carbodiimide (for the preparation of active esters, Bodansky, The Practice of Peptide Synthesis, (1984)).

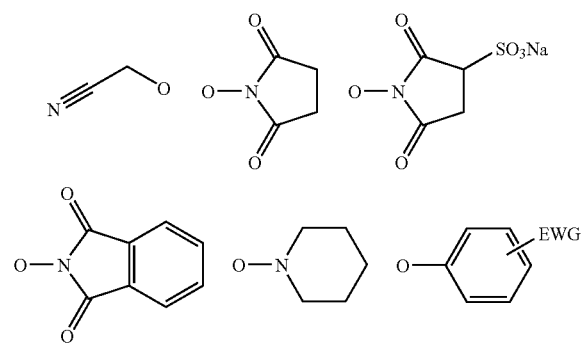

Preferably Z is hydroxysuccinimide or a substituted derivative thereof. Suitable derivatives include carboxylate or sulfonate, particularly preferably sulfonate (present, for example, the form of a sodium salt). The presence of these substituents can serve to enhance the solubility of hydroxysuccinimide-containing compounds of general formula (I) in, for example, water, or other appropriate solvents.

The linker compound, preferably of formula (I) or (II) as described herein, is linked to an amine-terminated solid surface.

The coupling reagent is an uronium or a phosphonium based coupling reagent which is only used for the in situ activation of compounds of formula (I) when Z=OH (for a review, Albericio et al., METHODS IN ENZYMOLOGY, 289, 104 (1997)). 1-Hydroxybenzotriazole esters which are generally too reactive to isolate, are probably the intermediates in the activation of compounds of formula (I) with such peptide coupling reagents (see the general formulas). Furthermore, it is also possible to generate these active esters by using carbodiimide (such as dicyclohexylcarbodiimide (DCC), diisopropylcarbodiimide (DIC) and 1-(3-dimethylaminopropyl)-3-ethylcarbodiimide hydrochloride (EDC)) and 1-hydroxybenzotriazole (HOBt) as system reagent.

General Formula III

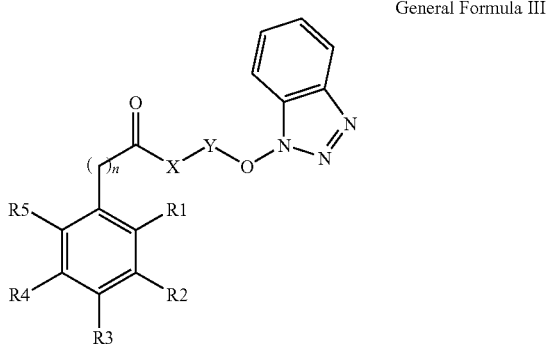

-continued

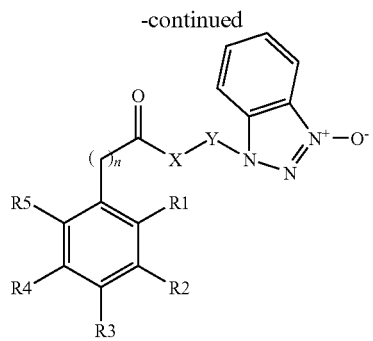

Interestingly, the methodology can also be applied to the polysulfonic acid derivatives.

The derivatization reaction is achieved by applying either a solution (in an anhydrous, non-volatile aprotic solvent such as dimethylformamide (DMF), dimethylsulfoxide (DMSO), or N-methylpyrrolidone (NMP)) of reactive polycarboxylic acid derivative (compounds of formula (I) when Z≠OH) or a mixture of free linker compound and coupling reagent (when Z=OH) to the amine-terminated solid surface (e.g., aminosilanated glass). Furthermore, the use of an excess of tertiary base (such as diisopropylethylamine (DIEA), triethylamine (TEA), N-ethylmorpholine (NEM) or N-methylmorpholine (NMM)) is essential for an efficient amidification. The reaction is typically conducted at room temperature for 30 minutes to 3 hours depending on the used mode of activation (nature of linker compound and coupling reagent) and results in the formation of one or two peptidic bonds between the amine-terminated surface and the polycarboxylic acid derivative. The active esters (especially the NHS derivatives) are prepared in good yields by using carbodiimide (DCC, DIC or EDC) as condensing reagent between polycarboxylic acid and the corresponding alcohol.

The strategy outlined above permits the use of many different polycarboxylic acids. We have determined by screening a large number of chemicals that best results are obtained using the aromatic compounds described by the general formula I, especially benzene-1,3,5-triacetic acid (BTA) and benzene-1,3,5-tricarboxylic acid (trimesic acid, TMA):

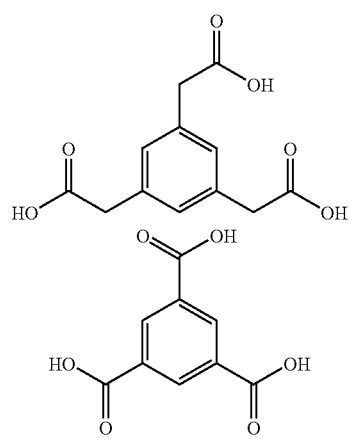

These benzene derivatives yield excellent results by providing carboxylated solid surface with good properties (high loading capacity, good electrostatic properties and hydrophilic character) which permit optimal immobilization and hybridization of nucleic acids. Such results can be explained by the specific geometry of these tricarboxylic acids. Indeed, the third $CO_2H$ group has a perpendicular orientation with regard to the two others. Consequently, only one or two $CO_2H$ groups is involved in the acylation of the surface-bound amino-groups and the others remain free for the covalent immobilization of biomolecules. Due to the increased tendency of the latter compound to hydrolyze, better results are obtained when upon conversion of aromatic acids into corresponding active esters (especially the NHS and HOBt esters). Concerning the preparation of the NHS esters, the use of different molar ratio between the tricarboxylic acid and the carbodiimide/alcohol reagent system provides a set of active species which exhibit one, two or three activated $CO_2H$ groups. Such compounds are either isolated or generated in the organic solvent used for the carboxylation reaction, immediately prior to use. However, preliminary experiments have clearly shown that the ester of BTA (or TMA) with all the three carboxylic groups activated by NHS are poorly soluble in the non-volatile aprotic solvents (i.e., DMF). Limited solubility in the solvent of such activated molecules (precipitation) makes that they are not available anymore for the carboxylation of the glass surface. Consequently, the activation of one or two $CO_2H$ groups of BTA (or TMA) seems to be the best strategy to achieve a clean and efficient chemical modification of the amine-terminated solid surfaces.

Alternatively, it is possible, and in certain circumstances, is preferred, that esters of BTA or TMA (or other compounds of formula (I)) may be activated with, preferably, NHS (or sulfo NHS) in the presence of coupling agents, such as EDC which triester preparations do not result in precipitation.

In situ activation of BTA (or TMA) by an uronium or a phosphonium based coupling reagent (such as benzotriazol-1-yloxytris(dimethylamino)phosphonium hexafluorophosphate (BOP)) may be used, which is less time-consuming than the protocols relying on synthesis of corresponding active esters (NHS and related compounds).

Carboxylation of the solid surface usually relies on direct application of a mixture of tricarboxylic acid (BTA or TMA), BOP (NHS, or related coupling reagents) and tertiary base to the amine-terminated solid surface. After washings with anhydrous solvents, the resulting carboxylated solid surface may contain some residual carboxylic groups in the "active" form. Consequently, reactions with various functional groups (amines, thiols, alcohols, phenols) of organic molecules, biomolecules, and others, may be possible without further carboxylic acid activation step. On the contrary, a short hydrolysis (with aqueous sodium bicarbonate) of the surface, immediately after the carboxylation reaction, provides a sodium carboxylate layer (highly hydrophilic), able to react with certain organic molecules, or biomolecules, only in the presence of a suitable coupling reagent.

Alternatively, when practicing the various methods of the invention, it is possible to attach appropriate (organic) molecules, e.g. biomolecules (preferably polynucleotides) which preferably contain an amino group, to a surface which has been treated with a molecule of formula (I) as described herein without a hydrolytic step immediately hereinbefore described which forms a sodium carboxylate layer as.

An example of how it is possible to attach appropriate (organic) molecules, e.g. biomolecules (preferably polynucleotides) which preferably contain an amino group, to a surface which has been treated with a molecule of formula (I), which is preferred, involves attaching a triester of BTA or TMA, such as an NHS triester or sulfo NHS triester (these are particularly preferred) to a amino-terminated support, preferably with the use of a coupling agent, advantageously EDC, so as to connect the molecule to the support so as to leave one or two esters unaffected (i.e. not having served to provide the point(s) at which the molecule of formula (I) is attached to the surface of the solid support). This mono or diester may then be reacted directly with the organic molecule so as to attach it to the solid support.

According to the present invention a method for preparing the linker compound comprising preparing the compound in a manner known per se is provided.

The present invention further provides a method for modifying an amino-terminated surface of a solid support with carboxy groups, preferably the solid support is glass, a polymer, a metal, a semiconductor or an insulator, particularly preferred the surface is an amine-terminated siloxane surface, comprising the steps of:

a) providing an amino-terminated surface; and
b) contacting the surface with a compound according to the compound of general formula (I) as described herein, (including compounds of general formula (II)) under conditions allowing the formation of an amide bond between a carboxy group of the compound of general formula (I) and the amino group of the solid surface.

Preferably, a coupling reagent is present. Further preferably, the coupling reagent comprises an uronium- or phosphonium-based coupling reagent.

The coupling reagent may also preferably comprise benzotriazol-b 1-yloxytris(dimethylamino)phosphonium hexafluorophosphate (BOP).

According to a preferred embodiment the coupling reagent comprises a carbodiimide, preferably the carbodiimide is dicyclohexylcarbodiimide, diisopropylcarbodiimide or 1-(3-dimethylaminopropyl)-3-ethylcarbodiimide hydrochloride. Particularly preferably the coupling agent is a carbodiimide which is 1-(3-dimethylaminopropyl)-3-ethylcarbodiimide hydrochloride.

According to a preferred embodiment in step b) an excess of a tertiary base is added, preferably the tertiary base is diisopropylethylamine, triethylamine, N-ethylmorpholine or N-methylmorpholine.

Preferably, in step b) additionally hydroxycinnamic acid, e.g. 4-hydroxycinnamic acid, is added.

Further preferably, in step b) the amount of the compound is limiting, preferably such that not all amino groups of the solid support are carboxylated.

According to a further aspect of the present invention a carboxy-terminated solid surface obtainable by the method according to the present invention is provided.

According to a further aspect a method for conjugating an amino-group containing substrate to an amino-terminated surface of a solid support is provided comprising:

a) performing the steps as defined above to obtain a carboxy-terminated surface of a solid support; and
b) contacting the amino-group containing substrate with the carboxy-terminated surface of the solid support of step a) under conditions allowing the formation of an amide bond between the carboxy group of the surface of the solid support and the amino group of the amino-group-containing substrate.

Preferably, in step b) a coupling reagent as defined above is present. Further preferably, in step b) a tertiary base as defined above is present. Preferably, the amino-group containing substrate is derived from nucleotides, amino acids, sugars, oligomers or polymers thereof.

REFERENCES CITED

Prior Art

U.S. Patent Documents
U.S. Pat. No. 6,319,674 (Fulcrand et al.) discloses derivatization of aminosilanized glass slides with 1,4-phenylene diisothiocyanate PCT Publications
WO 01/42495 A2 (Melnyk et al.) discloses a method for immobilization of nucleic acids on a solid support.

Other Publications
Adessi, C. et al. "Solid phase DNA amplification: characterisation of primer attachment and amplification mechanisms" *Nucleic Acids Research*, 28, e87, (2000).
Beaucage, S. L. "Strategies in the preparation of DNA oligonucleotide arrays for diagnostic applications" Current Medicinal Chemistry, 8 (2001), pp. 1213-1244.
Pirrung, M. C. "How to Make a DNA Chip" *Angewandte Chemie International Edition*, 41 (2002) pp. 1276-1289, and references cited herein.

REFERENCES CITED

Detailed Description

U.S. Patent Documents
U.S. Pat. No. 5,955,612 (Ahlem et al.) describes the preparation of new fluorescent labeling reagents derived from Texas Red®.

Other Publications
Bodansky, M. s and Bodansky, A., The Practice of Peptide Synthesis, (1984).
Albericio et al., "Coupling reagents and activation" *Methods in Enzymology*, 289, (1997) pp. 104-126.

The invention is illustrated in the following Experimental Section. It will be understood that the examples hereinafter are intended to be illustrative of the invention and in no way limitative of it.

EXPERIMENTAL SECTION

1. Preparation of the di-succinimidyl ester of benzene-1,3,5-tricarboxylic acid (trimesic acid, TMA) (Compound 1)

The following compound was prepared:

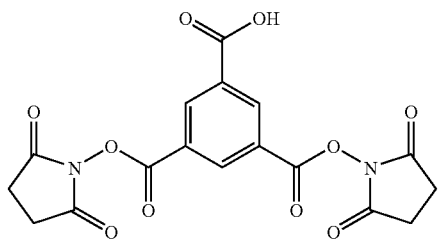

Benzene-1,3,5-tricarboxylic acid (0.5 g, 2.38 mmol) and N-hydroxysuccinimide (0.822 g, 7.14 mmol) were dissolved in 8 ml of dry THF. After cooling to 4° C. with an ice bath, DCC (1.473 g, 7.14 mmol) was added immediately, leading to the precipitation of dicyclohexylurea (DCU). The reaction vessel was then brought to room temperature and stirred for 2 hours. The DCU solid was removed by filtration and washed with dry THF (2×5 ml). The filtrate was concentrated to afford the desired compound as a white foam which was subsequently dried under high vacuum (0.508 g, yield 53%) and stored under an argon atmosphere. The structure of Compound 1 was confirmed by electrospray mass spectrometry (ESI-MS): m/z 402.86 [M–H]⁻. The moderate yield of the Compound 1 may be explained by the formation of the tri-succinimidyl ester of TMA (Compound 2) which precipitates with the DCU solids.

Compound 2 has the following structure:

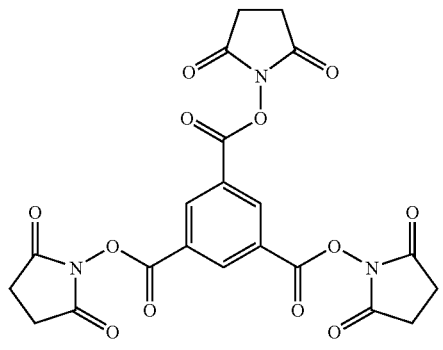

As mentioned above, an alternative strategy is the preparation of Compound 1 immediately prior to use without its isolation from the crude reaction mixture. THF is replaced by DMF, the latter being a suitable solvent for the carboxylation reaction.

2. Preparation of the di-succinimidyl ester of benzene-1,3,5-triacetic acid (BTA) (Compound 3)

The following compound was prepared following the general synthetic procedure given above for TMA:

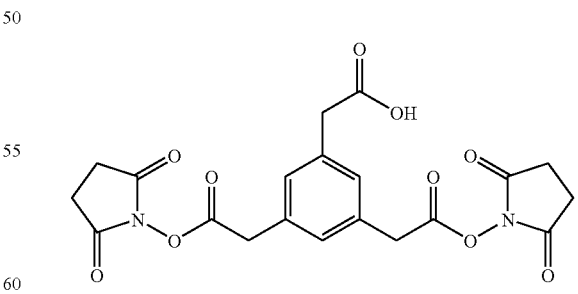

As described for Compound 1, Compound 3 can be generated in DMF solution immediately prior to use. Because of its increased hydrophobicity, the tri-succinimidyl ester of BTA (Compound 4) is removed by centrifugation (or filtration) since it usually precipitates with the DCU solids.

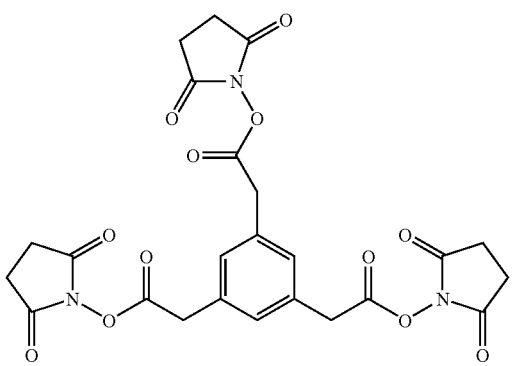

3. Conversion of Surface Terminated with an Amine Functionality to a Surface Terminated with the Carboxylate Functionality (DCC/NHS/DIEA Protocol)

Figure 1:
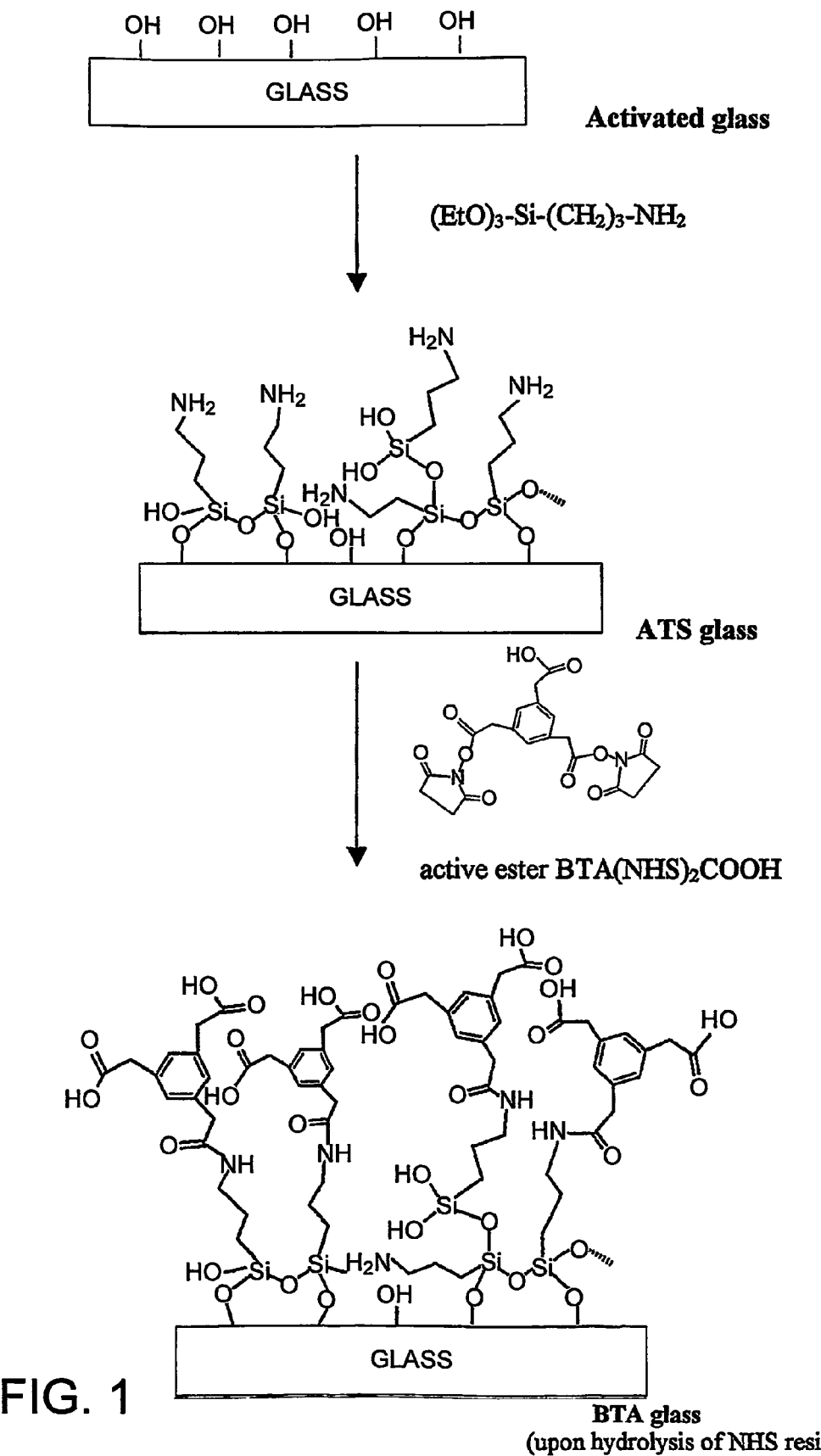
FIG. 1 shows the main steps in the preparation of BTA glass.

Main steps in the preparation of carboxylated BTA glass are shown in FIG. 1.

A. Glass Activation and Aminosilanization

Glass slides were first etched in a 1M NaOH solution, preferably in the presence of detergent (i.e., HellmanexII), which resulted in highly hydroxylated glass surface. Activated glass slides were then treated in an acid solution in water in order to remove hydroxide anion. Some additional glass etching was done in 50% sulfuric acid solution in water. The protocol for glass activation as used here is similar to that reported by Adessi et al. 2000, except for the fact that the time of glass slide treatment in 1M HCl has been reduced from 12 h to 1 h. Glass activation was done in 3 steps: i) 0.1% HellmanexII/1M NaOH solution (1 hour), ii) 1M HCl solution, 1 hour, iii) 50% $H_2SO_4$ (1 hour). Activated glass slides were extensively washed following each activation treatment in Millipore quality water (5 min). Final wash of slides in water was followed by their rinsing in absolute ethanol, and drying in the dessicator for 20 minutes (under vacuum). Silanization of hydroxylated glass slides (a batch of 8 slides) prepared as described above was preferably done in the silanization tank containing 5% 3-aminopropyltriethoxylsilane solution in acetone (1 hour). Aminosilanized slides (ATS) were then washed 3× in 100 ml of anhydrous acetone (5 minutes per wash, mild shaking), rinsed with ethanol and dried under the stream of $N_2$. ATS slides should be stored in the dessicator under vacuum before further use.

B. The Synthesis of Tri-Succinimidyl Ester of BTA and Carboxylation of ATS Glass Slides BTA (60.5 mg, 0.24 mmol) and N-hydroxysuccinimide (99.4 mg, 0.86 mmol) were dissolved in 1 ml of dry DMF and DCC (149.6 mg, 0.725 mmol) was added immediately, which resulted in the precipitation of DCU. The reaction vessel was stirred at room temperature for 2 hours. The DCU solid was removed by centrifugation (10000 rpm for 5 minutes) and a solution of DIEA (34.2 µl, 0.20 mmol) in dry DMF (0.965 ml) was added to the crude NHS ester mixture just before applying the solution the to aminosilanized ATS glass slides. 100 µl of the resulting solution was sandwiched between two ATS glass slides (32 ATS-silanized glass slides were carboxylated at once). Carboxylation of ATS slides was typically performed at room temperature for 3 hours. The glass slides were then washed successively with DMF and ethanol and dried with a stream of $N_2$. Hydrolysis of the residual ester groups on the BTA glass surface was done in a glass flask containing 5% $NaHCO_3$, pH 8.8 (100 ml per 8 BTA glass slides) for 15 minutes. BTA-derivatized glass slides were then washed with deionized water, followed by wash in anhydrous ethanol and dried with a stream of $N_2$.

C. Preparation of Glass Modified with Mixed —COOH/—OH Groups

Procedure for the preparation of glass surface containing mixed —COOH/—OH groups is similar to that described in Section 3B of the Experimental Part, however, 4-hydroxycinnamic acid (HPA) is admixed to BTA solution, followed by DCC/DIEA-catalyzed coupling to the aminosilanized ATS glass in DMF. BTA:HPA ratio may be varied from 0 to 100% and resulting mixtures may be then applied between the two ATS slides in face-to-face configuration. Reaction time of 3 hours was typically kept as in the case of BTA glass slides. Such —COOH/—OH films are expected to decrease the strength of molecular adsorption on glass surface due to electrostatic type of interactions between the ionized carboxylate groups and positively charged biomolecules (i.e., proteins). Mixed —COOH/—NH2 films on glass surfaces may be obtained following a partial carboxylation of the aminosilanized ATS glass.

4. Conversion of Surface Terminated with an Amine Functionality to a Surface Terminated with the Carboxylate Functionality (BOP/DIEA Protocol)

This conversion is achieved using TMA and BOP as coupling reagent. Five ATS-silanized glass slides prepared as above were reacted with a 50 mM solution of TMA (5.25 mg), a 250 mM solution of DIEA (21.4 µl) and a 50 mM solution of BOP in 0.5 ml of dry DMF for 30 min at room temperature. The glass slides are washed successively with DMF and ethanol and dried with a stream of $N_2$. After hydrolysis in a glass flask containing 100 ml of 5% $NaHCO_3$ (pH 8.8), TMA-derivatized glass slides were washed with deionized water and ethanol and dried with a stream of $N_2$.

5. Quality Control Procedure for the Carboxyl-Terminated Solid Surfaces

Coupling of sulforhodamine 101 sulfonylhexanediamine (Texas Red® derivative, Compounds 5a and 5b, a mixture of the two mono-sulfonamide isomers prepared using the synthetic procedure described in U.S. Pat. No. 5,955,612) The staining method described herein relies on the immobilization of amine-containing dye on the carboxylated surface and allows to determine the degree of carboxylation of aminated solid surface. As mentioned above, the activation of the surface carboxyl residues with a suitable coupling reagent C is essential. The choice of the experimental conditions depends critically on the dye solubility as well as on the chemical stability of the "active" carboxylated surface in a given solvent. With this aim in view, the following non-commercially available amino derivative of Texas Red (mixture of isomers) was synthesized from sulforhodamine 101:

Compound 5A

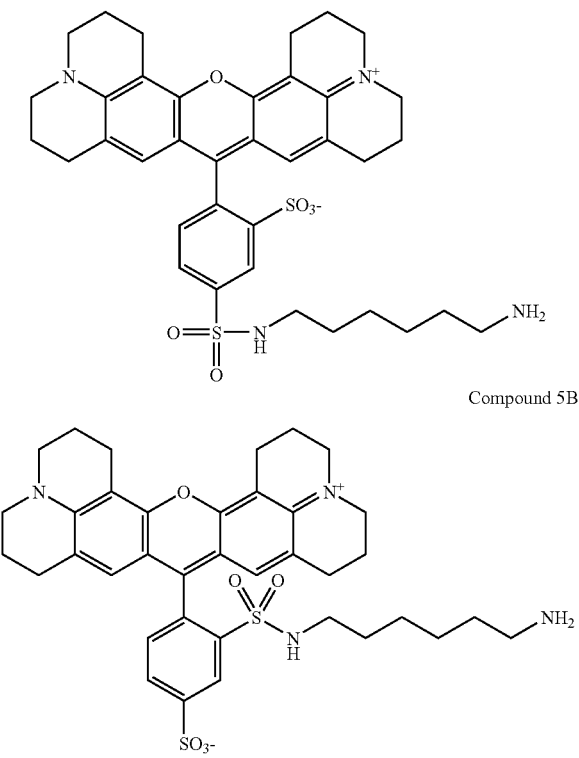

Compound 5B

The latter compound is able to react selectively with $CO_2H$ groups on the solid surface previously activated by an uranium- or a phosphonium-based coupling reagent (such as BOP) in the presence of a tertiary amine (DIEA or TEA) in an anhydrous non-volatile aprotic solvent (DMF, DMSO or NMP).

5A. Staining of Carboxyl-Terminated Slides with Amino-Texas Red

Eight BTA glass slides were reacted with a 0.7 mM solution of Compound 5 (Compound 5A+5B, 0.41 mg), a 2.1 mM solution of DIEA (0.3 μl) and a 0.7 mM solution of BOP (0.25 mg) in 0.8 ml of a mixture of dry DMSO/DMF (9/1, v/v) for 1 hour at room temperature (in the absence of light). The glass slides were washed successively with DMF followed by wash in absolute ethanol and dried with a stream of $N_2$. 100 μl of 5×SSC solution was pipetted on each amino-Texas Red-stained glass slide and covered with microscope coverslip glass. The fluorescence was measured in 5×SSC-using the inverted microscope AXIOVERT 200M (ZEISS, Germany) equipped with the 20× objective and Xf43 filter (Omega Optical, USA). As shown in the FIG. 3, the fluorescence intensity measured for Texas Red-stained BTA glass slides correlates well with the presence (or the lack) of carboxyl groups on the glass surface. Removal of the physisorbed Texas Red molecules from the aminosilanized glass was achieved in a solution of high ionic strength (stirred 1M NaCl, 12 h). Complete removal of the dye from the glass surface could not be achieved in pure DMF, ethanol, or in their aqueous solutions.

Procedure for the Removal of the Physisorbed Texas Red Molecules.

Amino-Texas Red-stained glass slides were rinsed with DMF, washed 2× in 100 ml DMF, rinsed by ethanol and dried under a stream of $N_2$. Stained slides were then dipped in 1M NaCl (200 ml) solution and stirred overnight (magnetic stirring bar placed in the center of the flask). This led to the removal of the physisorbed dye molecules from the amine-terminated ATS slide. However, fluorescence signal for the stained BTA slides remained at ~2100 a.u. (cf. FIG. 3). This clearly indicates that amino-Texas Red reacted with the surface carboxyl groups and got covalently attached to the BTA glass surface.

5B. Staining of Amine- and Carboxyl-Terminated Glass with NBD Derivatives

As discussed above, staining of carboxylated slides with amino-Texas Red introduces certain problems related to non-specific adsorption of the dye on the substrate surface. This is presumably due to strong electrostatic interactions between the partially ionized solid surface and charged Texas Red molecules in aqueous solutions. The latter renders washing of slides upon their staining relatively difficult, time consuming and, furthermore, introduces certain slide-to-slide irreproducibility.

Because of the above mentioned problems we have decided to search for a neutral (non-charged) fluorescent dye which would not interact with charged surfaces as is the case of Texas Red, or some other dyes used for DNA and/or protein labeling. Among other alternatives, 4-fluoro-7-nitrobenzofurazan (NBD-F) has been chosen as the best candidate for staining of aminosilanized ATS slides (see FIG. 4). On the other hand, ethylenediamine-NBD (NBD-$NH_2$, Compound 6) has been selected for the staining BTA slides (see FIG. 5). FIG. 6 illustrates that fluorescence signal for ATS, respectively, BTA slides correlates with the presence or absence of the surface carboxyl, respectively, amino groups. Residual signal in the case of BTA staining by NBD-F (FIG. 6A, negative control) may be explained as due to dye adsorption on aromatic residues within the BTA film. Non-specific fluorescence signal in the case of BTA slides has been shown to diminish upon a short (2 minutes) sonication of stained slides in DMF followed by ethanol wash. On the other hand, fluorescence intensity measured on ATS-NBD slides did not change following such sonication. Our staining experiments indicate that both NBD derivatives are ideally suited as Quality Control tool to follow batch-to-batch reproducibility of aminosilanization and carboxylation of glass slides. While in the case of ATS staining NBD-F is commercially (Fluka), amino derivative of 4-fluoro-7-nitrobenzofurazan (NBD-$NH_2$) was synthesized according to the following procedure.

Preparation of the Compound 6

The following compound was prepared:

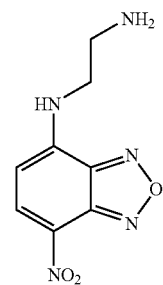

Ethylenediamine (206 µl, 3.07 mmol) was mixed in a 10 ml flask with 0.3 ml of dry DMF at 4° C. A solution consisting of 5.63 mg of NBD-F (0.03 mmol) in 0.1 ml of dry DMF (added dropwise over 5 minutes). The resulting reaction mixture was stirred at room temperature, in the absence of light, for 2 h. The solvents were then evaporated using the pump to dryness. The resulting orange oily residue was purified by chromatography on a silica gel (10 g) column with a step gradient of methanol (0 to 30%) in dichloromethane as the mobile phase. The appropriate fractions were pooled and then concentrated to dryness giving 2.56 mg of compound 6 as an orange solid (yield of 37%). TLC ($CH_2Cl_2/CH_3OH$ 80/20 v/v) $R_f$ 0.33 (compound 6), 1.00 (starting material, NBD-F); MS ($ES^+$) m/z 245.64 $(M+Na)^+$, 223.71 $(M+H)^+$.

Staining of the Aminosilanized ATS Slides with NBD-F

This protocol describes the quality control procedure that allows to follow batch-to-batch reproducibility of glass aminosilanization based on the reaction of 4-fluoro-7-nitrobenzofurazan (NBD-F) (Fluka, #47140) with the amine-terminated ATS glass. Fluorescence intensity of NBD-stained ATS slides is expected to correlate with the surface concentration of amino groups on the glass surface. Eight ATS-silanized glass slides are reacted with a 2.7 mM solution of NBD-F (0.26 mg) and a 5.5 mM solution of DIEA (0.5 µl) in dry DMF (100 µl for two slides placed face to face) for 1 hour at room temperature (in the absence of light). NBD-stained glass slides were then washed successively with DMF and ethanol and dried with a stream of nitrogen. The fluorescence was measured in the air using the inverted microscope AXIOVERT 200M (ZEISS) equipped with the 20× objective and Xf43 filter (Omega Optical, USA).

Staining of Carboxyl-Terminated Glass Slides with NBD-$NH_2$

The efficiency of the carboxylation of aminosilanized glass slides may be checked using the control procedure based on the coupling of amino derivative of 4-fluoro-7-nitrobenzofurazan (NBD-$NH_2$, Compound 6) to carboxyl groups on the glass surface activated with peptide coupling reagent BOP (benzotriazol-1-yloxytris(dimethylamino)phosphonium hexafluorophosphate Fluka, #12802) in the presence of a tertiary amine N,N-diisopropylethylamine (DIEA). The below described protocol allows to follow batch-to-batch reproducibility of glass carboxylation (staining of 8 carboxyl-terminated BTA slides).

Four BTA slides labeled #1-4 were placed on a clean glass support (17×14 cm glass plate). Two glass cylinders (4 mm in diameter) were placed under the slides at both extremities (in a form of rails) in order to avoid staining of slides on both sides.

0.34 mg NBD-$NH_2$ was weighed in the dark Eppendorf tube and dissolved in 600 µl DMF. 0.78 µl DIEA was then added and the resulting solution (solution A) was briefly vortexed. 0.67 mg BOP was weighed in another Eppendorf tube and dissolved by brief vortexing in 200 µl DMF (solution B). Solutions A and B were then mixed together and shortly vortexed (solution C). The solution C contained:

| 800 µl DMF |
| 0.78 µl DIEA |
| 0.67 mg BOP |
| 0.34 mg NBD-$NH_2$ (Compound 6)/ |
| 800 µl 1.9 mM NBD-$NH_2$ (1 eq.)/DIEA (3 eq.)/BOP solution in DMF |

100 µl of solution C were pipetted immediately on slide #1 and spread by placing the slide #2 on top of it. The same procedure was repeated for the slides #3-8. The staining reaction was let to proceed for 60 minutes in the absence of light. The glass slides were then washed successively with DMF and ethanol, dried with a stream of $N_2$ and kept under vacuum for at least 20 minutes (avoid aqueous solutions since NBD fluorescence is strongly quenched in the presence of water). The fluorescence for NBD-stained slides were taken in the air using the inverted microscope AXIOVERT 200M (ZEISS, Germany) equipped with the 20× objective and Xf43 filter (Omega Optical, USA).

6. Covalent Coupling of 5' $NH_2$—$C_6$-DNA to Carboxyl-Terminated BTA Glass

Figure 2:
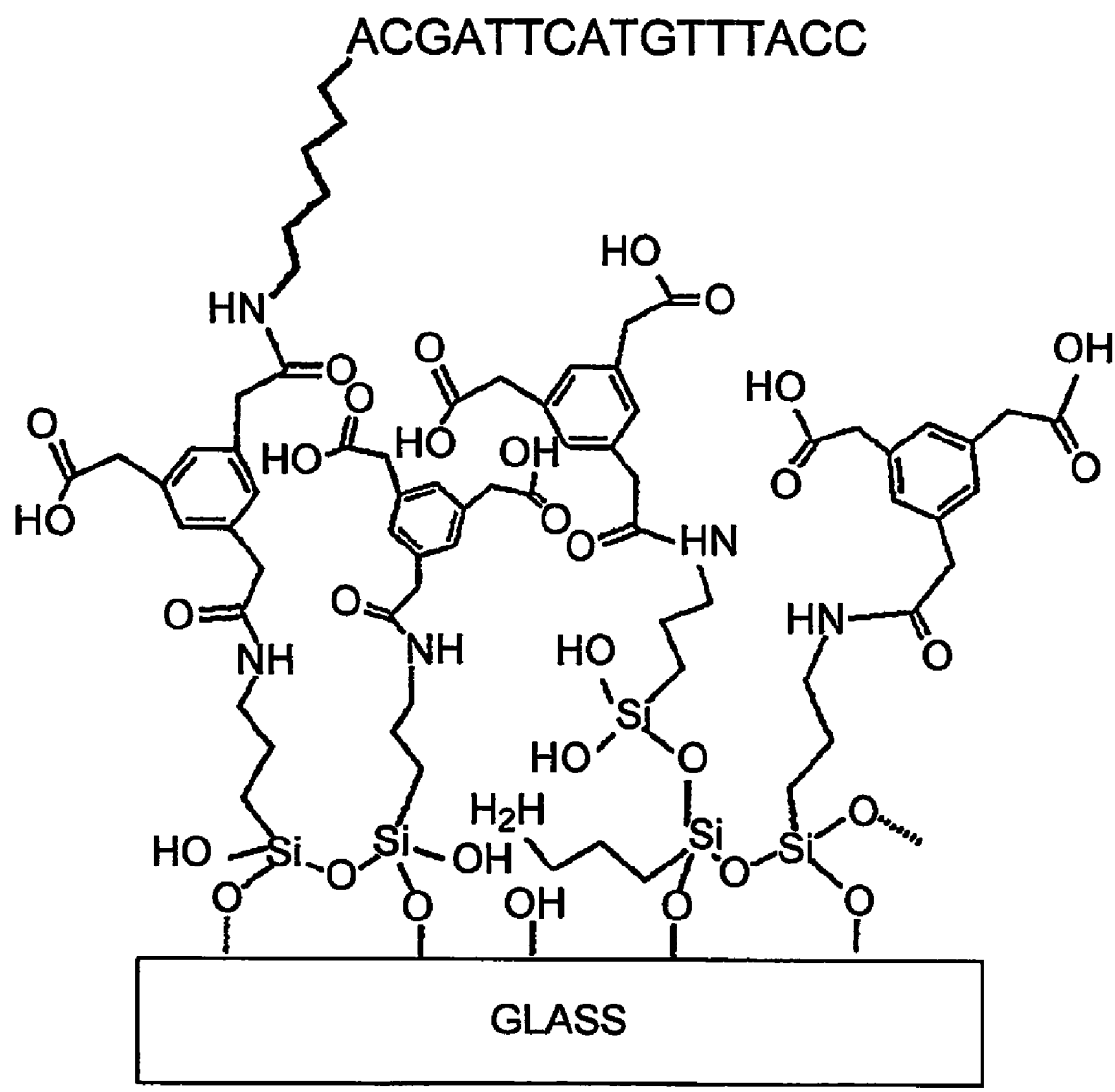
FIG. 2 shows the main steps in the EDC/MeImz-catalyzed immobilization of DNA on BTA glass.
Figure 2:
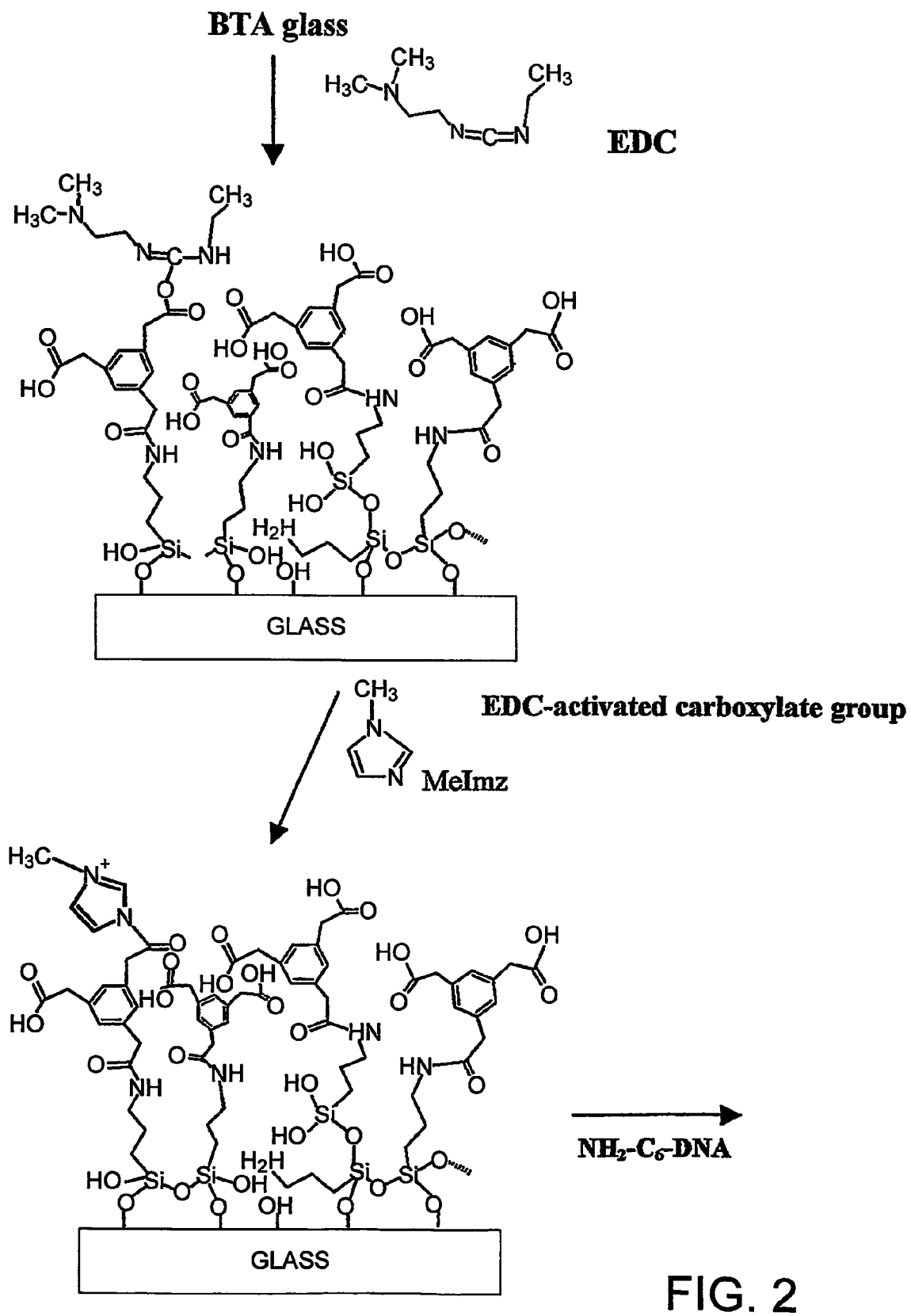

Main steps in the grafting of the 5'-aminated DNA to carboxylated BTA glass surface catalyzed by carbodiimide/methylimidazole are shown in FIG. 2. Hybridization of Texas Red-labeled DNA (24-mer) having complementary sequence to grafted DNA and specificity of surface hybridization are illustrated in the FIG. 7. FIGS. 7-8 show that hybridization signal decreases with decreasing DNA concentration in the grafting mix. The saturation coverage for grafted DNA primer on BTA glass was attained following the 1 h grafting at 50° C. for the bulk concentrations of DNA exceeding 1 µM (FIG. 8). FIG. 9 shows that the hybridization signal obtained on BTA slides, which reflects high surface coverage by DNA primers, is significantly higher as compared to that obtained on phenylene isothiocyanate slides (PDITC #1-4) prepared according to U.S. Pat. No. 6,319,674 and A. J. Thiel et al., Anal. Chem., 1997, 69:4948-4956), or that obtained on commercial carboxyl-terminated slides CAB-25C from CEL Associates, USA (CAB #1-4).

Grafting Protocol:

Grafting mix: 0.1-10 µM $P_1$ (34-mer), 10 mM EDC, 10 mM methylimidazole. Frame seal wells (Bioconcept, Switzerland) were fixed on BTA glass and filled with 25 µl of the Grafting Mix (on ice). Glass slides with spotted DNA were incubated at 50° C. for 10-60 minutes in a humid atmosphere. The grafting solution was removed with a pipette (the same side of the well was touched each time) and each well was washed 3 times with 0.1×SSC-0.1% Tween, and 3 times with 5×SSC solutions (1 minute each wash). Glass slides were gently shaken for 10 seconds at the end of each wash.

7. Solid Phase Amplification of DNA on BTA Glass and Formation of DNA Colonies

Solid phase DNA amplification according to PCT publications WO 98/44151 and WO 00/18957 requires covalent grafting through the 5' amino linkage of the two primers P1 and P2 (typically 20-30 nt) and larger in size (several hundred base pairs) DNA template 5'$NH_2$—P1-X-revP2 (X=variable sequence). DNA template contains at its 3' end a complementary sequence (revP2) to one of the primers. Solid phase amplification of the DNA template on a solid surface involves: i) denaturation of the template DNA, ii) annealing of its 3' end to P2 primer, iii) X-templated extention of the 3' end of P2 by thermostable DNA polymerase (i.e., by Taq polymerase) and formation of P2-revX-revP1 strand in a single amplification cycle. Under classical thermocycling conditions (typically 20-40 amplification cycles), both of the strands, namely, P1-X-revP2 and P2-revX-revP1 undergo denaturation, surface annealing and extention making use of both of covalently attached primers. In a process, the surface concentration of free DNA primers P1 and P2 diminishes while that of the template DNA increases. The amplified DNA template forms during the solid-phase amplification process well separated islands (several micrometers in size) called DNA colonies. The surface amplification of large number of co-grafted DNA templates having variable sequence X but primer-complementary sequence at their 5', respectively, 3' ends (as discussed above) allows formation of DNA colonies representing each template sequence. It is important in this respect that arching of the template DNA during the solid-phase DNA amplification requires relatively high surface densities of grafted primers (primer-to-primer spacing close to 10 nm). Such high densities of primers were achieved on BTA glass prepared as described in the previous sections.

FIG. 10 shows fluorescent image taken for double-stranded DNA colonies stained by SYBr GreenI (intercalating agent) prepared on carboxylated BTA glass. DNA primers and template DNA were grafted in BTA-carboxylated channels of the microfluidic device from 40 mM EDC/MeImz solution (50° C./30 minutes). Ratio between the grafted primers and template DNA (p/T) was kept 1:2000. DNA was amplified on BTA surface in a 40 amplification cycles using Taq DNA polymerase under conditions specified in the FIG. 10. The surface concentration of template DNA is increased under the latter conditions by ca. 1000-fold.

All patents, patent applications, and published references cited herein are hereby incorporated by reference in their entirety. While this invention has been particularly shown and described with references to preferred embodiments, it will be understood by those skilled in the art that various changes in form and details may be made without departing from the scope of the invention encompassed by the claims.

The invention claimed is:

1. A method for modifying an amino-terminated surface of a solid support with carboxy groups comprising the steps of:
   a) providing an amino-terminated surface; and
   b) contacting the surface with a compound of the general formula (I):

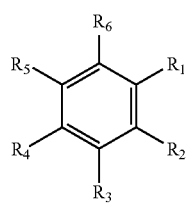

(I)

wherein at least three of $R_1$ to $R_6$ are, independent from each other, selected from $-(CH_2)_n-(C=O)-X-Y-Z$, and the remaining R groups are H; or $R_1$ and $R_6$ form a ring;

X is a group selected from $C_1$-$C_{10}$ alkyl, $C_1$-$C_{10}$ alkenyl, a $C_3$-$C_8$ cycloalkyl, aryl, heteroaryl, or a polyethylene glycol chain of the general form $(CH_2-CH_2-O)_m$, wherein m is an integer from 1 to 450, or X is a bond;
Y is a carbonyl group, or a bond;
Z is OH or an electron withdrawing group; and
n is an integer from 0 to 10,
under conditions allowing the formation of an amide bond between a carbon of a carboxy group of the compound of the general formula (I) and a nitrogen of the amino group of the solid surface.

2. A method for modifying an amino-terminated surface of a solid support with carboxy groups comprising the steps of:
   a) providing an amino-terminated surface; and
   b) contacting the surface with a compound of the general formula (I):

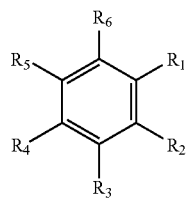

(I)

wherein:
(i) at least three of $R_1$ to $R_6$ are, independent from each other, selected from $-(CH_2)_n-(C=O)-X-Y-Z$ and the remaining R groups are H; or
(ii) $R_1$ and $R_6$ are together of formula $-(C=O)-Z'-(C=O)-$ so as to form a ring, at least one of $R_2$ to $R_5$ are, independent from each other, selected from $-(CH_2)_n-(C=O)-X-Y-Z$ and the remaining R groups are H;

X is a group selected from $C_1$-$C_{10}$ alkyl, $C_1$-$C_{10}$ alkenyl, a $C_3$-$C_8$ cycloalkyl, aryl, heteroaryl, or a polyethylene glycol chain of the general form $(CH_2-CH_2-O)_m$, wherein m is an integer from 1 to 450, or X is a bond;
Y is a carbonyl group, or a bond;
Z is OH or an electron withdrawing group;
Z' is O or S; and
n is an integer from 0 to 10, under conditions allowing the formation of an amide bond between a carbon of a carboxy group of the compound of the general formula (I) and a nitrogen of the amino group of the solid surface.

3. The method of claim 1, wherein the solid support is glass, a polymer, a metal, a semiconductor or an insulator.

4. The method of claim 3 wherein the solid support has an amine-terminated siloxane surface.

5. The method of claim 1, wherein n=0.

6. The method of claim 1, wherein n=1.

7. The method of claim 1, wherein n is an integer from 2 to 5.

8. The method of claim 1 wherein two of $R_1$ to $R_6$ are, independent from each other, selected from $-(CH_2)_n-(C=O)-X-Y-Z$; one of $R_1$ to $R_6$, independent from each other, is selected from $-(CH_2)_n-(C=O)-X-Y-OH$; wherein Z is an electron withdrawing group; and the remaining R groups are H.

9. The method of claim 1, wherein one of $R_1$ to $R_6$ is of formula $-(CH_2)_n-(C=O)-X-Y-Z$; two of $R_1$ to $R_6$, independent from each other, are selected from $-(CH_2)_n-(C=O)-X-Y-OH$; Z=electron withdrawing group and the remaining R groups are H.

10. The method of claim 1 wherein each of $R_1$, $R_3$ and $R_5$ are independently selected from $-(CH_2)_n-(C=O)-X-Y-Z$.

11. The method of claim 2, wherein Z' is O.

12. The method of claim 1, wherein the compound of general formula (I) is of the general formula (II):

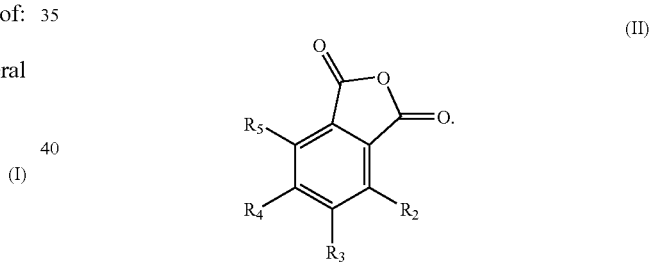

(II)

13. The method of claim 1 wherein Z is an electron withdrawing group.

14. The method of claim 1, wherein Z is a halogen atom selected from F, Cl and Br.

15. The method of claim 1, wherein Z is selected from phenoxy substituted by at least one strong electron withdrawing group, cyanomethoxy, O-succinimide or its sodium sulfonate derivative NHS or sulfo-NHS, O-phthalimide, and O-piperidine.

16. The method as claimed in claim 15, wherein Z is selected from:

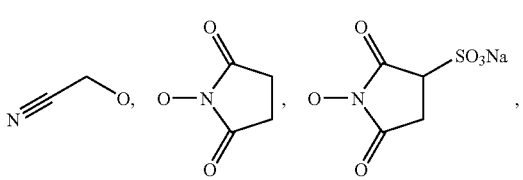

-continued

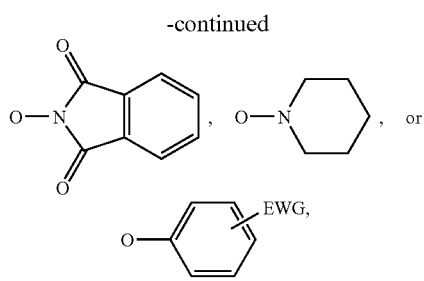

wherein EWG is an electron withdrawing group.

17. The method of claim 1, wherein the compound is trimesic acid or a mono-, di-, or tri-succinimidyl ester thereof, or the compound is benzene-1,3,5-triacetic acid or a mono-, di-, or tri-succinimidyl ester thereof.

18. The method of claim 17, wherein the compound is trimesic acid or a mono- or di-succinimidyl ester thereof, or the compound is benzene-1,3,5-triacetic acid or a mono- or di-succinimidyl ester thereof.

19. The method of claim 17, wherein the compound is a tri-succinimidyl ester of trimesic acid, or the compound is a tri-succinimidyl ester of benzene-1,3,5-triacetic acid.

20. The method of claim 17, wherein said succinimidyl ester is a substituted succinimidyl ester.

21. The method of claim 20 wherein said substituted succinimidyl ester is a sulfonate derivative of succinimide.

22. The method of claim 1 wherein a coupling reagent is present.

23. The method as claimed in claim 22, wherein the coupling reagent comprises an uronium- or phosphonium-based coupling reagent.

24. The method as claimed in claim 23, wherein the coupling reagent comprises benzotriazol-1-yloxytris (dimethylamino)phosphonium hexafluorophosphate (BOP).

25. The method as claimed in claim 22, wherein the coupling reagent comprises a carbodiimide.

26. The method as claimed in claim 25, wherein the carbodiimide is dicyclohexylcarbodiimide, diisopropylcarbodiimide or 1-(3-dimethylaminopropyl)-3-ethylcarbodiimide hydrochloride.

27. The method as claimed in claim 26, wherein the carbodiimide is 1-(3-dimethylaminopropyl)-3-ethylcarbodiimide hydrochloride.

28. The method of claim 1 wherein in step b) an excess of a tertiary base is added.

29. The method of claim 28, wherein the tertiary base is diisopropylethylamine, triethylamine, N-ethylmorpholine or N-methylmorpholine.

30. The method of claim 1 wherein in step b) additionally hydroxycinnamic acid is added.

31. The method of claim 1 wherein in step b) the amount of the compound is limited, whereby not all amino groups of the solid support may be carboxylated.

32. A solid surface obtainable by the method of claim 1.

33. The solid surface of claim 32 which is a carboxy-terminated solid surface.

34. A method for conjugating an amino-group containing substrate to an amino-terminated surface of a solid support comprising:
 i) performing the steps as defined in claim 1 to obtain a carboxy-terminated surface of a solid support; and
 ii) contacting the amino-group containing substrate with the carboxy-terminated surface of the solid support of step i) under conditions allowing the formation of an amide bond between the carboxy group of the surface of the solid support and the amino group of the amino-group-containing substrate.

35. The method of claim 34, wherein the amino group-containing substrate is derived from nucleotides, amino acids, sugars, oligomers or polymers thereof.

* * * * *